US011834714B2

(12) United States Patent
Shum et al.

(10) Patent No.: US 11,834,714 B2
(45) Date of Patent: Dec. 5, 2023

(54) DETECTION AND DIGITAL QUANTITATION OF MULTIPLE TARGETS

(71) Applicant: Enumerix, Inc., Palo Alto, CA (US)

(72) Inventors: Eleen Yee Lam Shum, San Carlos, CA (US); Hei Mun Christina Fan, Palo Alto, CA (US); Stephen P. A. Fodor, Palo Alto, CA (US); Janice Hoiyi Lai, Mountain View, CA (US); Jung Won Keum, Palo Alto, CA (US); Haeun Grace Lee, Palo Alto, CA (US)

(73) Assignee: ENUMERIX, INC., Palo Alto, CA (US)

( * ) Notice: Subject to any disclaimer, the term of this patent is extended or adjusted under 35 U.S.C. 154(b) by 0 days.

(21) Appl. No.: 18/085,217

(22) Filed: Dec. 20, 2022

(65) Prior Publication Data
US 2023/0193385 A1 Jun. 22, 2023

Related U.S. Application Data

(63) Continuation of application No. PCT/US2022/053413, filed on Dec. 19, 2022.

(60) Provisional application No. 63/291,813, filed on Dec. 20, 2021.

(51) Int. Cl.
C12Q 1/6876 (2018.01)
G01N 21/64 (2006.01)
G01N 33/542 (2006.01)

(52) U.S. Cl.
CPC ....... *C12Q 1/6876* (2013.01); *G01N 21/6428* (2013.01); *G01N 33/542* (2013.01); *C12Q 2600/156* (2013.01); *C12Q 2600/16* (2013.01); *G01N 2021/6439* (2013.01)

(58) Field of Classification Search
CPC ............ C12Q 1/6876; C12Q 2600/156; C12Q 2600/16; G01N 21/6428; G01N 33/542; G01N 2021/6439
See application file for complete search history.

(56) References Cited

U.S. PATENT DOCUMENTS

| 3,480,616 | A | 11/1969 | Osipow et al. |
| 3,644,333 | A | 2/1972 | Osipow et al. |
| 4,683,058 | A | 7/1987 | Lyman et al. |
| 5,216,033 | A | 6/1993 | Pereira et al. |
| 5,679,539 | A | 10/1997 | Hudson et al. |
| 5,688,940 | A | 11/1997 | Lyttle |
| 5,707,613 | A | 1/1998 | Hill |
| 5,753,241 | A | 5/1998 | Ribier et al. |
| 5,925,338 | A | 7/1999 | Karassik et al. |
| 6,120,778 | A | 9/2000 | Simonnet |
| 6,121,055 | A | 9/2000 | Hargreaves |
| 6,277,957 | B1 | 8/2001 | Hudson et al. |
| 6,379,682 | B1 | 4/2002 | Tchinnis et al. |
| 6,387,357 | B1 | 5/2002 | Chopra et al. |
| 6,403,069 | B1 | 6/2002 | Chopra et al. |
| 6,696,298 | B2 | 2/2004 | Cook et al. |
| 6,761,855 | B1 | 7/2004 | Cook et al. |
| 7,019,129 | B1 | 3/2006 | Cook et al. |
| 7,041,481 | B2 | 5/2006 | Anderson et al. |
| 7,041,841 | B1 | 5/2006 | Canich |
| 7,160,996 | B1 | 1/2007 | Cook |
| 7,344,701 | B2 | 3/2008 | Reddington et al. |
| 7,582,432 | B2 | 9/2009 | Cook et al. |
| 7,635,598 | B2 | 12/2009 | Cook et al. |
| 7,635,762 | B2 | 12/2009 | Cook et al. |
| 8,871,444 | B2 | 10/2014 | Griffiths et al. |
| 8,889,093 | B2 | 11/2014 | Malhotra et al. |
| 9,012,390 | B2 | 4/2015 | Holtze et al. |
| 9,029,083 | B2 | 5/2015 | Griffiths et al. |
| 9,039,273 | B2 | 5/2015 | Weitz et al. |
| 9,074,242 | B2 | 7/2015 | Larson et al. |
| 9,127,310 | B2 | 9/2015 | Larson et al. |
| 9,222,128 | B2 | 12/2015 | Saxonov et al. |
| 9,410,151 | B2 | 8/2016 | Link et al. |
| 9,446,360 | B2 | 9/2016 | Mazutis |

(Continued)

FOREIGN PATENT DOCUMENTS

| CN | 1089361 A | 7/1994 |
| CN | 2612943 Y | 4/2004 |

(Continued)

OTHER PUBLICATIONS

Shum et al, Next-Generation Digital Polymerase Chain Reaction: High-Dynamic- Range Single-Molecule DNA Counting via Ultrapartitioning, 2022, Anal. Chem., 2022, 94, 17868-17876. (Year: 2022).*

Lehnert et al, Fluorescence signal-to-noise optimization for real-time PCR using universal reporter oligonucleotides, 2018, Anal. Methods, 10, pp. 3444-3454 (Year: 2018).*

Shum et al Next-Generation Digital Polymerase Chain Reaction: High-Dynamic- Range Single-Molecule DNA Counting via Ultrapartitioning, Post art, Anal. Chem. 2022, 94, 1768-17876 (Year: 2022).*

Liao et al, Three-dimensional digital PCR through light-sheet imaging of optically cleared emulsion, 2020, PNAS, 117, 25628-25633 (Year: 2020).*

Lehnert et al, Fluorescence signal-to-noise optimization for real-time PCR using universal reporter oligonucleotides, 2018, 10, 3444-3454 (Year: 2018).*

(Continued)

*Primary Examiner* — Narayan K Bhat
(74) *Attorney, Agent, or Firm* — Wilson Sonsini Goodrich & Rosati

(57) ABSTRACT

The disclosure provides compositions, methods, and systems for implementation of highly multiplexed molecular diagnostic assays involving color combinatorics, stimulus-responsive probes, tandem probes, conjugated polymer probes, and other mechanisms for increasing the number of targets that can be simultaneously detected in a digital assay. Multiplexed detection of targets is achieved in a rapid manner, with respect to sample partitioning and target detection using multiple color channels for detection. Implementation of methods described also achieve detection with significantly improved signal-to-noise ratio (SNR) values.

22 Claims, 19 Drawing Sheets

(56) References Cited

U.S. PATENT DOCUMENTS

| | | |
|---|---|---|
| 9,562,837 B2 | 2/2017 | Link |
| 9,610,239 B2 | 4/2017 | Feng et al. |
| 9,788,564 B2 | 10/2017 | Bromley |
| 9,803,240 B2 | 10/2017 | Cook et al. |
| 10,301,310 B2 | 5/2019 | Reddington et al. |
| 10,519,485 B2 | 12/2019 | Cook et al. |
| 10,537,503 B2 | 1/2020 | Lei et al. |
| 10,619,192 B2 | 4/2020 | Chiu et al. |
| 10,927,419 B2 | 2/2021 | Fan et al. |
| 11,034,677 B2 | 6/2021 | Sanchez |
| 11,162,136 B1 | 11/2021 | Fan et al. |
| 11,242,558 B2 | 2/2022 | Fan et al. |
| 11,447,817 B2 | 9/2022 | Fan et al. |
| 11,542,546 B2 | 1/2023 | Fan et al. |
| 2004/0081633 A1 | 4/2004 | Mercier et al. |
| 2006/0128883 A1 | 6/2006 | Garrison et al. |
| 2008/0182910 A1 | 7/2008 | Qiu et al. |
| 2009/0239308 A1 | 9/2009 | Dube et al. |
| 2010/0173394 A1 | 7/2010 | Colston, Jr. et al. |
| 2012/0322058 A1 | 12/2012 | Regan et al. |
| 2014/0272996 A1 | 9/2014 | Bemis |
| 2016/0199491 A1 | 7/2016 | Cook et al. |
| 2018/0092847 A1 | 4/2018 | Schutt et al. |
| 2018/0136114 A1 | 5/2018 | Delattre et al. |
| 2019/0255531 A1 | 8/2019 | Hindson et al. |
| 2019/0358625 A1 | 11/2019 | Huang et al. |
| 2020/0037638 A1 | 2/2020 | Faraci et al. |
| 2021/0241857 A1 | 8/2021 | Fraley et al. |
| 2021/0324459 A1* | 10/2021 | Fan ................. B01L 3/5023 |
| 2022/0170085 A1 | 6/2022 | Fan et al. |
| 2022/0280941 A1 | 9/2022 | Fan et al. |

FOREIGN PATENT DOCUMENTS

| | | |
|---|---|---|
| CN | 1758405 A | 4/2006 |
| CN | 103145346 A | 6/2013 |
| CN | 103320514 A | 9/2013 |
| CN | 103649813 A | 3/2014 |
| CN | 104111242 A | 10/2014 |
| CN | 104237186 A | 12/2014 |
| CN | 104284970 A | 1/2015 |
| CN | 104407436 A | 3/2015 |
| CN | 104741156 A | 7/2015 |
| CN | 104741158 A | 7/2015 |
| CN | 104815709 A | 8/2015 |
| CN | 105854965 A | 8/2016 |
| CN | 106053346 A | 10/2016 |
| CN | 106076443 A | 11/2016 |
| CN | 107653337 A | 2/2018 |
| CN | 207062288 U | 3/2018 |
| CN | 109060736 A | 12/2018 |
| CN | 109439788 A | 3/2019 |
| GB | 2103611 A | 2/1983 |
| JP | 3568846 B2 | 9/2004 |
| WO | WO-2008079274 A1 | 7/2008 |
| WO | WO-2009149449 A1 | 12/2009 |
| WO | WO-2015097185 A1 | 7/2015 |
| WO | WO-2017215428 A1 | 12/2017 |
| WO | WO-2017215429 A1 | 12/2017 |
| WO | WO-2020001529 A1 | 1/2020 |
| WO | WO-2020144480 A1 | 7/2020 |
| WO | WO-2021138078 A1 | 7/2021 |
| WO | WO-2021241857 A1 | 12/2021 |
| WO | WO-2023003453 A1 | 1/2023 |
| WO | WO-2023034531 A1 | 3/2023 |

OTHER PUBLICATIONS

Huang et al.: Centrifugal micro-channel array droplet generation for highly parallel digital PCR. Lap on a Chip 17(2):235-240 (2017).

Lehnert et al.: Fluorescence signal-to-noise optimisation for real-time PCR using universal reporter oligonucleotides. Anal. Methods 10:3444-3454 (2018).

Liao et al.: Combination of fluorescence color and melting temperature as a two-dimensional label for homogeneous multiplex PCR detection. Nucleic Acids Research 2013, 41:7 e76 (2013).

Maar et al.: Expanded Droplet Digital PRC Multiplexing Capability Using Two Different Strategies. Bio-Rad Laboratories, Inc., Bulletin 7204 (2019).

McMahon et al.: Multiplexed Single Intact Cell Droplet Digital PCR (MuSIC ddPCR) Method for Specific Detection of Enterohemorrhagic *E. coli* (EHEC) in Food Enrichment Cultures. Frontiers in Microbiology 8:332 (2017).

PCT/CN2017/085891 International Search Report and Written Opinion dated Sep. 1, 2017.

PCT/CN2017/085892 International Search Report and Written Opinion dated Aug. 11, 2017.

PCT/CN2019/093241 International Search Report and Written Opinion dated Oct. 8, 2019.

PCT/US2021/027353 International Search Report and Written Opinion dated Aug. 13, 2021.

PCT/US2022/53413 International Search Report and Written Opinion May 8, 2023.

Schlenker et al.: Virtual Fluorescence Color Channels by Selective Photobleaching in Digital PCR Applied to the Quantification of KRAS Point Mutations. Analytical Chemistry 93(30):10538-10545 (2021).

Schulman et al.: Formation of microemulsions by amino alkyl alcohols. Ann N Y Acad Sci. 92:366-371 doi:10.1111/j.1749-6632. 1961.tb44987.x (1961).

Sun et al.: Refractive index matching and clear emulsions. International Journal of Cosmetic Science 27(6):355-356 (2005). First published: Nov. 18, 2005 https://doi.org/10.1111/j.1467-2494.2005. 00290_3.x.

Vladisavljević et al.: Production of uniform droplets using membrane, microchannel and microfluidic emulsification devices. Microfluidics and Nanofluidics 13:151-178 (2012).

Wright et al.: The use of cell-free fetal nucleic acids in maternal blood for non-invasive prenatal diagnosis. Human Reproduction Update 15(1):139-151 (2009).

Yamashita et al.: Generation of monodisperse cell-sized microdroplets using a centrifuge-based axisymmetric co-flowing microfluidic device. Journal of Bioscience and Bioengineering 119(4): 492-495 (2014).

Yanny et al.: Miniscope3D: optimized single-shot miniature 3D fluorescence microscopy. Light: Science & Applications 9:171 (2020).

Zhao et al.: Massive droplet generation for digital PCR via a smart step emulsification chip integrated in a reaction tub. Analyst 2021, 146:15568 (2021).

Zhu et al., Highly sensitive and quantitative detection of rare pathogens through agarose droplet microfluidic emulsion PCR at the single-cell level. Lab on a Chip 12(20):3907-3913 (2012).

* cited by examiner

EXEMPLARY/REPRESENTATIVE ASSAY COMPONENTS

Low Partition System

High Partition System

○ Target A
● Target B
◐ Target C
◉ Indeterminate due to Doublet

| TARGET | Allele | Color Combination |
|---|---|---|
| 1 | 1 | ○ |
| 1 | 2 | ● |
| 2 | 1 | ○ (dashed) |
| 2 | 2 | ◎ |
| 3 | 1 | ◉ (shaded) |
| 3 | 2 | ○ ● |
| 4 | 1 | ○ ○ (dashed) |
| 4 | 2 | ○ ◎ |
| 5 | 1 | ○ ◉ |
| 5 | 2 | ● ○ (dashed) |
| 6 | 1 | ● ◎ |
| 6 | 2 | ● ◉ |
| 7 | 1 | ○ (dashed) ◎ |
| 7 | 2 | ○ (dashed) ◉ |
| 8 | 1 | ◎ ◉ |
| 8 | 2 | ○ ● ○ (dashed) |
| 9 | 1 | ○ ● ◎ |
| 9 | 2 | ○ ● ◉ |
| 10 | 1 | ● ○ (dashed) ◎ |
| 10 | 2 | ● ○ (dashed) ◉ |
| 11 | 1 | ○ (dashed) ◎ ◉ |
| 11 | 2 | ○ ● ○ (dashed) ◎ |
| 12 | 1 | ● ○ (dashed) ◎ ◉ |
| 12 | 2 | ○ ● ◎ ◉ |
| 13 | 1 | ○ ○ (dashed) ◎ ◉ |
| 13 | 2 | ○ ● ○ (dashed) ◎ ◉ |

Example Target Tagged with
Tandem Probes

Example Emulsion
With Targets Tagged using
Color Combinatorics

Local amplitude changes at same partition locations are usable to differentiate targets

PROBES:

Positive identification of Target 1 (e.g., within a partition)
Based on detection of signals from Fluorophores 1 and 2

Positive identification of Target 2 (e.g., within a partition)
Based on detection of signals from Fluorophores 1, 2, and 3

DETECTION AND DIGITAL QUANTITATION OF MULTIPLE TARGETS

CROSS-REFERENCE

This application is a continuation of International Patent Application No. PCT/US2022/053413 filed 19 Dec. 2022, which claims the benefit of U.S. Provisional Application No. 63/291,813 filed on 20 Dec. 2021, each of which applications is incorporated in its entirety herein by this reference.

TECHNICAL FIELD

The disclosure generally relates to systems, methods, and compositions for digital counting of multiple targets in a highly-multiplexed manner.

BACKGROUND

Detection of target material in a multiplexed manner contributes to rapid generation of diagnostic results. Compositions and methods used to label multiple genetic targets and/or variations, such as single nucleotide polymorphisms (SNPs), copy number variations (CNVs), insertions, deletions, and/or other loci of interest, methylation markers, gene expression markers, small and microRNA markers, genome modification markers, and other markers can contribute to generation of diagnoses and/or support interpretation of assay results, which can be used to provide healthcare or otherwise improve outcomes in other fields of interest. Multiplexed detection of targets can also provide value in research or other non-clinical settings, with or without evaluation and processing of live human or mammalian biological material, and without the immediate purpose of obtaining a diagnostic result of a disease or health condition.

In applications, digital quantitation of multiple targets, through genotyping, can further be useful in relation to characterizations (e.g., of relative abundance) in many fields. Multiplexing for detection and digital quantitation of multiple targets using partition-based systems (e.g., as in digital PCR) has, however, been traditionally limited by the number of partitions available, partition format (e.g., 3D format vs. 1D or 2D formats), number of colors available for analysis (e.g., in relation to dye/probe tagging limitations, in relation to detection limitations of imaging subsystems, etc.) for detection, high apparatus costs, operation in a high-occupancy regime requiring statistical error correction factors for assessment of results, material costs, and other factors. For instance, in traditional PCR multiplexing reactions, targets are differentiated using one probe per target conjugated with dyes of different excitation and emission spectra, which restricts multiplexing to systems that can cope with multiple emission spectra for detection of fluorescence from the different probe dyes. Furthermore, signal overlap associated with operation in a high-occupancy regime typically results in reduced precision in quantitation and other aspects of sample characterization. Such traditional approaches include methods to compensate for deficiencies (e.g., with use of computational tools involving virtual partitioning).

Furthermore, approaches to multiplexing have been based on creating unique endpoints for detection (e.g., with respect to tagging by unique probes and/or primers, followed by performance of reactions and detection), with signal amplitude-based differentiation of tagged targets. In more detail, amplitude-based multiplexing achieves unique endpoints by varying primer and/or probe concentrations to produce unique endpoints for target detection, and probe-mixing multiplexing achieves unique endpoints by mixing probes at desired concentration in order to segregate clusters of targets (in multi-axis plots), post-detection of signals by a particular modality. Limitations of existing approaches can, however, be overcome by the systems, methods, and compositions of the disclosure described in following sections.

As such, there is a need for innovation in fields related to systems, compositions, and methods for multiplexed detection and quantitation of targets.

SUMMARY OF THE INVENTION

Currently, platforms, methods, and compositions for performing multiplexed analyses involve significant infrastructure investment (e.g., in relation to microfluidic platform and detection platform aspects); however, such technologies are limited in relation to: number of targets that can be detected simultaneously; mechanism by which different targets are differentially detected (e.g., as in mechanisms involving primarily signal amplitude-based detection); ability to provide multiplexing capability with a high degree of accuracy for partitioning technologies where the partitions are arranged three-dimensionally (3D) in bulk format (e.g., in a packed configuration in three dimensions); ability to provide multiplexing for partitioning technologies involving an extremely high number of partitions (e.g., greater than 1 million partitions) for digital analyses; and other factors in the context of multidimensional digital analyses.

Accordingly, this disclosure describes embodiments, variations, and examples of systems, methods, and compositions for digital detection of a large number of targets in a high-performance, efficient, and accurate manner, and with less complex instrumentation.

An aspect of the disclosure provides compositions, methods, and systems for implementation of highly multiplexed molecular diagnostic assays involving color combinatorics, stimulus-responsive probes, tandem probes, conjugated polymer probes, and other mechanisms for increasing the number of targets that can be simultaneously detected in a digital assay. As described in more detail below, combinations of mechanisms can provide a number of targets that can be differentially detected according to $n!/[r! (n-r)!]$, where n represents the number of available colors, and r represents the number of selected colors from the number of available colors. Permutations of mechanisms can provide a number of targets that can be differentially detected according to $n!/[(n-r)!]+n$, where n represents the number of available colors, and r represents the number of selected colors from the number of available colors. In examples, the numbers of targets that can be differentially tagged and detected from a single sample and within a single assay run can be greater than 10 targets, greater than 15 targets, greater than 20 targets, greater than 25 targets, greater than 30 targets, greater than 35 targets, greater than 40 targets, greater than 45 targets greater than 50 targets, greater than 55 targets, greater than 60 targets, greater than 65 targets, greater than 70 targets, greater than 75 targets, greater than 80 targets, greater than 85 targets, greater than 90 targets, or greater than 100 targets, with optical detection of signals from targets.

Differential detection is achieved in part due to the high number of partitions involved when using the technologies described, where distribution of sample targets across partitions results in low occupancy of partitions by targets, and large partition numbers contribute to significantly low percentages of doublets (e.g., single partitions occupied by two targets), triplets (e.g., single partitions occupied by three targets), or other forms of multi-plets (single partitions occupied by multiple targets). In particular, successful multiplexing at this level is attributed to the high degree of partitioning (with achievable numbers of generated partitions described) and extremely low occupancy (with achievable percent occupancies described), such that multiple molecules from the target molecules of interest have a minimal (or zero) probability of occupying the same partition as another target molecule. In such a high-partition and low-occupancy regime, there is no competition associated with multiple target molecules per partition, and the platform is not subject to problems related to differences in PCR efficiency between different target molecules.

In the context of digital multiplexed analyses, the disclosure also provides systems, methods, and compositions that can achieve a high dynamic range, due to the number of partitions involved and occupancy of the partitions by targets of the sample. In examples, the systems, methods, and compositions can provide a dynamic range of: over 4 orders of magnitude from a lower count capability to a higher count capability (e.g., at least $10^4$), over 5 orders of magnitude from a lower count capability to a higher count capability (e.g., at least $10^5$), over 6 orders of magnitude from a lower count capability to a higher count capability (e.g., at least $10^6$), over 7 orders of magnitude from a lower count capability to a higher count capability (e.g., at least $10^7$), or greater, for sample volumes described. In examples, the systems, methods, and compositions can achieve quantification of targets over a 4-log dynamic range, over a 5-log dynamic range, over a 6-log dynamic range, over a 7-log dynamic range, or greater, for sample volumes described.

For partitions arranged in bulk (e.g., in close-packed format, in the form of droplets of an emulsion) within a closed container, the systems, methods. and compositions described can provide discernable signals from individual partitions, with readout performed using multiple color channels (e.g., 2 color channels, 3 color channels, 4 color channels, 5 color channels, 6 color channels, 7 color channels, etc.) corresponding to light sources and optics involved in detection, with suitable signal-to-noise (SNR) characteristics in relation to background fluorescence.

For multiplexed analyses, methods described involve detection of signals from a large number of partitions, where detected signals correspond to a set of color combinatorics paired with targets of a set of targets potentially represented in the sample and contained within partitions of the set of partitions, and wherein the set of targets has a total number greater than the number of color channels used to detect colors corresponding to the set of color combinatorics. In examples, the set of color combinatorics involves combinations of up to 3 colors, up to 4 colors, up to 5 colors, up to 6 colors, up to 7 colors, or greater (from each of the set of partitions), where each combination of colors has a corresponding target associated with the respective combination.

In one embodiment, the set of partitions involves droplets of an emulsion within a closed container, and the set of color combinatorics involves combinations of up to 3 colors, up to 4 colors, up to 5 colors, up to 6 colors, up to 7 colors, etc. detectable from each of the set of partitions. Additionally or alternatively, multiplexing involving stimulus-responsive materials can expand the number of targets that can be differentially tagged and detected by a factor equal to the number of states through which probes used to tag targets can transition. Additionally or alternatively, multiplexing involving materials that exhibit Foerster resonance energy transfer (FRET) behavior can expand the number of targets that can be differentially tagged and detected by a factor equal to the number of FRET capable probes used.

The disclosure also provides compositions that produce significantly improved signal-to-noise (SNR) values with reduced background, in relation to detection techniques described below (e.g., based on lightsheet imaging, etc.) for partitions arranged in bulk in 3D. In examples, target signals can be at least $10^2$ greater than background noise signals, $10^3$ greater than background noise signals, $10^4$ greater than background noise signals, $10^5$ greater than background noise signals, $10^6$ greater than background noise signals, $10^7$ greater than background noise signals, or better. Background noise can be attributed to fluorescence from adjacent partitions and adjacent planes of the set of planes of partitions in the context of emulsion digital PCR, or attributed to other sources with closely-positioned partitions.

In examples associated with reaction materials described and used for droplet digital PCR, determining the target signal value can include: for each plane of a set of planes of partitions under interrogation (e.g., by lightsheet detection, by another method of detection, etc.): determining a categorization based upon a profile of positive partitions represented in a respective plane, determining a target signal distribution and a noise signal distribution specific to the profile, and determining a target signal intensity and a noise signal intensity for the respective plane. Here, the target signal value can be an average value (or other representative value) of the target signal intensities determined from the set of planes, and the background noise signal value can be an average value (or other representative value) of the noise signal intensities determined from the set of planes.

The disclosure also provides oligonucleotide compositions and designs for multiplexed assays (e.g., locked nucleic acid (LNA) assays, KASP® assays, Taqman® assays, etc.). Such improved oligonucleotides improve sample processing, with respect to primer cleanup/removal, reduction of background, implementation of compatible forward and reverse primers for direct multiplexed assays (e.g., PCR), implementation of checks for complementarity of amplicons to non-self probes (i.e., in both sense and antisense strands), implementation of checks for complementarity of primers to probes (i.e., in both sense and antisense strands), generation of positive and negative controls for a clinical workflow, establishment of limits of detection (LoDs) and other metrics for NIPT ultraPCR assays, and/or other improvements.

Examples of partition generation methods can include generating an extremely high number of droplets (e.g., greater than 5 million droplets, greater than 6 million droplets, greater than 7 million droplets, greater than 8 million droplets, greater than 9 million droplets, greater than 10 million droplets, greater than 15 million droplets, greater than 20 million droplets, greater than 25 million droplets, greater than 30 million droplets, greater than 40 million droplets, greater than 50 million droplets, greater than 100 million droplets, etc.) within a collecting container having a volumetric capacity (e.g., less than 50 microliters, from 50 through 100 microliters and greater, etc.), where droplets have a characteristic dimension (e.g., from 1-50 micrometers, from 10-50 micrometers, etc.) that is relevant for digital analyses, target detection, individual molecule partitioning, or other applications.

In relation to occupancy, embodiments, variations, and examples of partitioning are conducted in a manner such that each partition has one or zero molecules, such that the partitions are characterized as having low occupancy (e.g., less than 15% occupancy of partitions by individual molecules, less than 14% occupancy of partitions by individual molecules, less than 13% occupancy of partitions by individual molecules, less than 12% occupancy of partitions by individual molecules, less than 11% occupancy of partitions by individual molecules, less than 10% occupancy of partitions by individual molecules, less than 9% occupancy of partitions by individual molecules, less than 8% occupancy of partitions by individual molecules, less than 7% occupancy of partitions by individual molecules, less than 6% occupancy of partitions by individual molecules, less than 5% occupancy of partitions by individual molecules, less than 4% occupancy of partitions by individual molecules, etc.).

In examples, the systems, methods, and compositions described can be used to generate 50,000 counts per target for each of a set of targets of interest, 60,000 counts per target for each of a set of targets of interest, 70,000 counts per target for each of a set of targets of interest, 80,000 counts per target for each of a set of targets of interest, 90,000 counts per target for each of a set of targets of interest, 100,000 counts per target for each of a set of targets of interest, 120,000 counts per target for each of a set of targets of interest, 130,000 counts per target for each of a set of targets of interest, 140,000 counts per target for each of a set of targets of interest, 150,000 counts per target for each of a set of targets of interest, 160,000 counts per target for each of a set of targets of interest, 170,000 counts per target for each of a set of targets of interest, 180,000 counts per target for each of a set of targets of interest, 190,000 counts per target for each of a set of targets of interest, 200,000 counts per target for each of a set of targets of interest, 210,000 counts per target for each of a set of targets of interest, 220,000 counts per target for each of a set of targets of interest, 230,000 counts per target for each of a set of targets of interest, 240,000 counts per target for each of a set of targets of interest, 250,000 counts per target for each of a set of targets of interest, 260,000 counts per target for each of a set of targets of interest, 270,000 counts per target for each of a set of targets of interest, 280,000 counts per target for each of a set of targets of interest, 290,000 counts per target for each of a set of targets of interest, 300,000 counts per target for each of a set of targets of interest, or other counts per target for each of a set of targets of interest.

Compositions, methods, and systems described can further involve use of a single primer with tandem adapters or multiple primers used to tag targets with probes. Multiplexed primers structured to flank target-specific probes that encode for different targets can be used. Multiplexed primer compositions can be configured for 20-plex amplification of loci of interest for each a set of targets being analyzed, 30-plex amplification of loci of interest for each a set of targets being analyzed, 40-plex amplification of loci of interest for each a set of targets being analyzed, 50-plex amplification of loci of interest for each a set of targets being analyzed, 60-plex amplification of loci of interest for each a set of targets being analyzed, 70-plex amplification of loci of interest for each a set of targets being analyzed, 80-plex amplification of loci of interest for each a set of targets being analyzed, 90-plex amplification of loci of interest for each a set of targets being analyzed, 100-plex amplification of loci of interest for each a set of targets being analyzed, or greater.

Relatedly, an aspect of the disclosure provides embodiments, variations, and examples of devices and methods for rapidly generating partitions (e.g., droplets from a sample fluid, droplets of an emulsion) and distributing nucleic acid material (e.g., multiplexed target detection) across partitions, where, the device includes: a first substrate defining a reservoir comprising a reservoir inlet and a reservoir outlet; a membrane coupled to the reservoir outlet and comprising a distribution of holes; and a supporting body comprising an opening configured to retain a collecting container in alignment with the reservoir outlet. During operation, the first substrate can be coupled with the supporting body and enclose the collecting container, with the reservoir outlet aligned with and/or seated within the collecting container. During operation, the reservoir can contain a sample fluid (e.g., a mixture of nucleic acids of the sample and materials for an amplification reaction), where application of a force to the device or sample fluid generates a plurality of droplets within the collecting container at an extremely high rate (e.g., of at least 200,000 droplets/minute, of at least 300,000 droplets/minute, of at least 400, droplets/minute, of at least 500,000 droplets/minute, of at least 600,000 droplets/minute, of at least 700,000 droplets/minute, of at least 800,000 droplets/minute, of at least 900,000 droplets/minute, of at least 1 million droplets/minute, of at least 2 million droplets/minute, of at least 3 million droplets/minute, of at least 4 million droplets/minute, of at least 5 million droplets/minute, of at least 6 million droplets per minute, etc.), where the droplets are stabilized in position (e.g., in a close-packed format, in equilibrium stationary positions) within the collecting container.

An aspect of the disclosure provides embodiments, variations, and examples of a method for rapidly generating partitions (e.g., droplets from a sample fluid, droplets of an emulsion) within a collecting container at an extremely high rate, each of the plurality of droplets including an aqueous mixture for a digital analysis, wherein upon generation, the plurality of droplets is stabilized in position (e.g., in a close-packed format, at equilibrium stationary positions, etc.) within a continuous phase (e.g., as an emulsion having a bulk morphology defined by the collecting container). In aspects, partition generation can be executed by driving the sample fluid through a distribution of holes of a membrane, where the applied force can be one or more of centrifugal (e.g., under centrifugal force), associated with applied pressure, magnetic, or otherwise physically applied.

In relation to a single-tube workflow in which the collecting container remains closed (e.g., the collecting container has no outlet, there is no flow out of the collecting container, to avoid sample contamination), method(s) can further include transmitting heat to and from the plurality of droplets within the closed collecting container according to an assay protocol. In relation to generation of emulsions having suitable clarity (e.g., with or without refractive index matching), method(s) can further include transmission of signals from individual droplets from within the closed collecting container, for readout (e.g., by an optical detection platform, by another suitable detection platform).

Where method(s) include transmitting heat to and from the plurality of droplets, within the closed container, the droplets are stable across a wide range of temperatures (e.g., 1° C. through 95° C., greater than 95° C., less than 1° C.) relevant to various digital analyses and other bioassays, where the droplets remain consistent in morphology and remain unmerged with adjacent droplets.

The disclosure generally provides mechanisms for efficient capture, distribution, and labeling of target material (e.g., DNA, RNA, miRNA, proteins, small molecules, single analytes, multianalytes, etc.) in order to enable genomic, proteomic, and/or other multi-omic characterization of materials, in parallel and in a multiplexed manner, for various applications.

In examples, the approach discussed is designed around a simple workflow to enable deployment to local and decentralized laboratories. First, samples are carried end-to-end in the same PCR tube for user convenience and to minimize sample contamination. Second, ultra-partitioning and PCR amplification can be performed in standard laboratory equipment such as a swing bucket centrifuge and thermal cycler, lowering the infrastructure cost for ultraPCR adoption. However, compositions of the disclosure can also be utilized in coordination with various technologies for isolating material in single-molecule format (e.g., by use of wells, by use of droplets, by use of other partitioning elements, etc.).

Another aspect of the present disclosure provides a non-transitory computer readable medium comprising machine executable code that, upon execution by one or more computer processors, implements any of the methods above or elsewhere herein.

The disclosure provides compositions, methods, and systems for multiplexed detection of targets that can provide value in research or other non-clinical settings, with or without evaluation and processing of live human or mammalian biological material, and without the immediate purpose of obtaining a diagnostic result of a disease or health condition.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. The present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entireties for all purposes and to the same extent as if each individual publication, patent, or patent application was specifically and individually indicated to be incorporated by reference.

Furthermore, where a range of values is provided, it is understood that each intervening value, between the upper and lower limit of that range and any other stated or intervening value in that stated range is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

BRIEF DESCRIPTION OF THE DRAWINGS

FIG. 3C depicts a schematic of example color combinations for differential detection and quantitation of targets.

FIG. 3D depicts a schematic of example color combinations for differential detection and quantitation of targets.

DETAILED DESCRIPTION OF THE INVENTION(S)

Figure 1A:
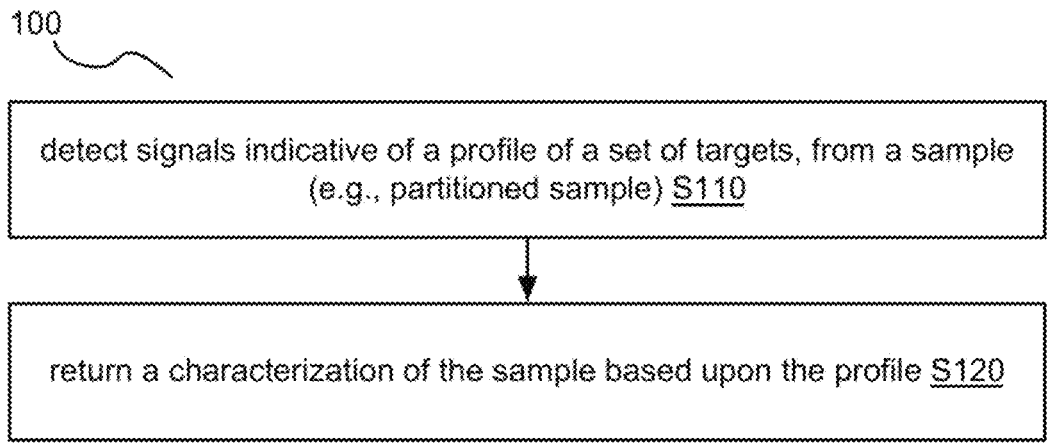
FIG. 1A depicts a flowchart of an embodiment of a method for multiplexed detection and digital quantitation of targets.
Figure 1B:
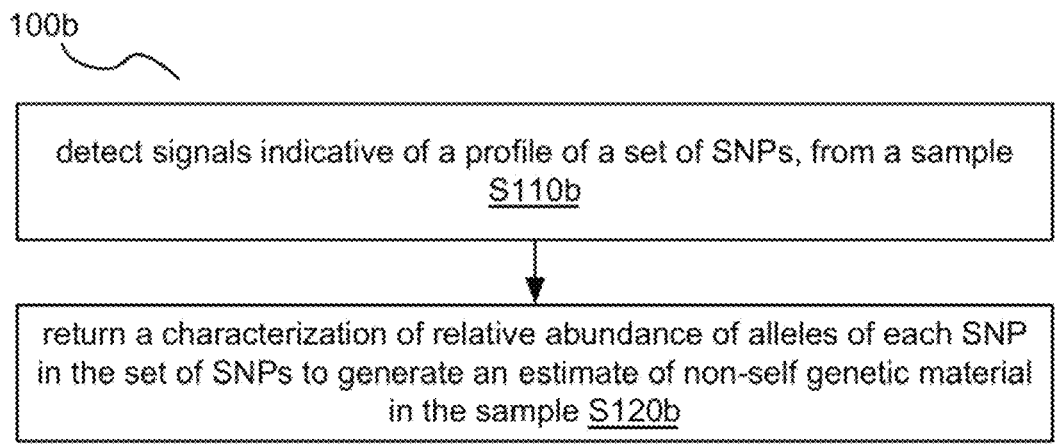
FIG. 1B depicts a flowchart of a variation of a method for multiplexed detection and digital quantitation of targets, with applications in characterizing non-self genetic material from a sample.

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed.

1. General Overview

The systems, methods, and compositions described can confer several benefits over conventional systems, methods, and compositions.

In particular, the systems, methods, and compositions of the present disclosure enable detection and digital quantitation of a set of targets having a number much greater than the number of channels (e.g., color channels, fluorescence detection channels) available for detection. Multiplexed detection involving a greater number of targets than available color channels for detection is based upon one or more of: color combinatorics, stimulus-responsive probes, tandem probes, conjugated polymer probes, and other mechanisms for increasing the number of targets that can be simultaneously detected in a digital assay. Such functionality is attributed to operation in a regime involving low occupancy of a large number of partitions, such that there is an extremely low probability of overlap between target template molecules within individual partitions. Large partition numbers contribute to significantly low percentages of doublets (e.g., single partitions occupied by two targets), triplets (e.g., single partitions occupied by three targets), or other forms of multi-plets (single partitions occupied by multiple targets). As such, signals from different amplified target templates distributed across individual partitions can be differentially detected and analyzed in relation to performance of digital assays.

In the context of emulsion digital PCR with partitions retained in bulk within a container, the systems, methods, and compositions of the present disclosure achieve improved signal-to-noise (SNR) with respect to detection of signals from a partition surrounded in three dimensions by other partitions also potentially emitting signals, where the partitions are interrogated by a three dimensional imaging technique. Some assay chemistries (e.g., such as EvaGreen® chemistry, SYBR® chemistry) are less appropriate for such applications as they can yield high levels of background noise that reduce assay performance.

In the context of digital multiplexed analyses, the disclosure also provides systems, methods, and compositions that can achieve a high dynamic range, due to the number of partitions involved and occupancy of the partitions by targets of the sample. In examples, the systems, methods, and compositions can provide a dynamic range of: over 4 orders of magnitude from a lower count capability to a higher count capability (e.g., at least $10^4$), over 5 orders of magnitude from a lower count capability to a higher count capability (e.g., at least $10^5$), over 6 orders of magnitude from a lower count capability to a higher count capability (e.g., at least $10^6$), over 7 orders of magnitude from a lower count capability to a higher count capability (e.g., at least $10^7$), or greater, for sample volumes described. In examples, the systems, methods, and compositions can achieve quantification of targets over a 4-log dynamic range, over a 5-log dynamic range, over a 6-log dynamic range, over a 7-log dynamic range, or greater, for sample volumes described.

For partitions arranged in bulk (e.g., in close-packed format, in the form of an emulsion) within a closed container, the systems, methods. and compositions described can provide discernable signals from individual partitions, with readout performed using multiple color channels (e.g., 2 color channels, 3 color channels, 4 color channels, 5 color channels, 6 color channels, 7 color channels, 8 color channels, etc.), with suitable signal-to-noise (SNR) characteristics in relation to background fluorescence.

For multiplexed analyses, methods described involve detection of signals from a large number of partitions, where detected signals correspond to a set of color combinatorics paired with targets of a set of targets potentially represented in the sample and contained within partitions of the set of partitions, and wherein the set of targets has a total number greater than the number of color channels used to detect colors corresponding to the set of color combinatorics. In examples, the set of color combinatorics involves combinations of up to 3 colors, up to 4 colors, up to 5 colors, up to 6 colors, up to 7 colors, or greater, where each combination of colors has a corresponding target associated with the respective combination.

In one embodiment, the set of partitions involves droplets of an emulsion within a closed container, and the set of color combinatorics involves combinations of up to 3 colors, up to 4 colors, up to 5 colors, up to 6 colors, up to 7 colors, etc. detectable from each of the set of partitions. Additionally or alternatively, multiplexing involving stimulus-responsive materials can expand the number of targets that can be differentially tagged and detected by a factor equal to the number of states through which probes used to tag targets can transition. Additionally or alternatively, multiplexing involving materials that exhibit Foerster resonance energy transfer (FRET) behavior can expand the number of targets that can be differentially tagged and detected by a factor equal to the number of FRET capable probes used.

In the context of emulsion digital PCR with the numbers of partitions described, such multiplexed assay design aspects described can produce significantly improved signal-to-noise (SNR) values with reduced background, in relation to detection techniques described below (e.g., based on light-sheet imaging, etc.). In examples, the ratio of target signals (e.g., median target signals) to noise (e.g., median background noise from other partitions and/or planes of partitions) can be greater than $10^2$, greater than $10^3$, greater than $10^4$, greater than $10^5$, greater than $10^6$, greater than $10^7$, greater than $10^8$, greater than $10^9$, greater than $10^{10}$, or any intermediate value. Background noise can be attributed to fluorescence from adjacent partitions and adjacent planes of the set of planes of partitions in the context of emulsion digital PCR, or attributed to other sources with closely-positioned partitions. In examples, upon processing a sample with the processing materials, noise (e.g., median noise from other partitions and/or from other planes of partitions) can be reduced in relation to target signals by a factor of at least $10^{-2}$, $10^{-3}$, $10^{-4}$, $10^{-5}$, $10^{-6}$, $10^{-7}$, $10^{-8}$, $10^{-9}$, $10^{-10}$, or any intermediate value.

In variations, processing materials of the systems, methods, and compositions of the present disclosure described can include: a primer set comprising a common primer and a target-specific primer (or set of target-specific primers) structured to interact with the target region, the target-specific primer having a common adapter sequence, a fluorophore-labeled oligonucleotide corresponding to the common adapter sequence, the fluorophore-labeled oligonucleotide comprising a fluorophore configured to transmit a target signal if the target region is amplified, and a probe additive reagent structured to reduce background noise (e.g., from adjacent partitions and planes of partitions within the container, as described). The common primer can be a forward primer or a reverse primer. The target-specific primer can be a forward primer or a reverse primer. In specific examples, processing materials can include Taqman® probes (e.g., dual-labeled hydrolysis probes). In specific examples, processing materials can include molecular beacons or similar probe structures (e.g., probes with hairpin structures), where such probes are quenched by quenchers at regions opposite respective fluorophores when the probe is not bound to a target or in an extended configuration.

The systems, methods, and compositions of the present disclosure can provide high degrees of multiplexing for detection and digital counting of different targets in parallel, using color combinatorics in a non-sequencing-based system (e.g., non-next generation sequencing (NGS)-based system), in a limiting dilution regimen. In specific examples, the systems, methods, and compositions can provide high degrees of multiplexing for characterization of different targets in parallel, using color combinatorics in a partition-based PCR system capable of providing an ultra-high number of partitions, thereby reducing/eliminating signal overlap and contributing to unambiguous assignment of partition contents for detection and digital quantitation.

In more detail, the systems, methods, and compositions can confer the benefit of enabling performance of ultra-high multiplexed target detection using a partitioning system and methods of sample processing configured to provide a high number of partitions (e.g., more than 100,000 partitions, more than 200,000 partitions, more than 500,000 partitions, more than 1 million partitions, more than 10 million partitions, more than 20 million partitions, more than 30 million partitions, more than 50 million partitions, more than 100 million partitions, etc.) with low-occupancy (e.g., less than 10% occupancy, less than 8% occupancy, less than 5% occupancy, etc.) of partitions by targets. In particular, use of a low-occupancy platform involving high numbers of partitions provides a regime where the probability of encountering a falsely-labeled multi-color partition associated with one of a set of targets is very low. Such a regime allows a high number of targets to be uniquely labeled by at least one color at low error.

In various applications, methods and system of the application provide functionality for assaying samples for a panel of SNPs, CNVs, insertions, deletions, targets associated with other loci of interest, and/or other suitable components. Evaluation of samples is performed in a multiplexed manner/in parallel, instead of detecting targets one-by-one in separate reactions.

In various applications, the systems, methods, and compositions of the disclosure can evaluate samples for a panel of SNPs (e.g., 50 common SNPs, less than 50 common SNPs, greater than 50 common SNPs) without requiring sequencing of an individual first to determine the target panel. Common SNPs are those that have allele frequency of 1% or more (e.g., from 30-60% allele frequency) in the population.

In one specific use case, the methods, systems, and compositions of the disclosure can be used to determine an amount of non-self vs. self genetic material in a sample mixture (e.g., from relative abundance calculations), where self genetic material originates from a subject, and non-self genetic material originates from another subject, and both the self genetic material and non-self genetic material are mixed within the same sample. Determination of non-self vs. self genetic material can have specific uses in one or more of: non-invasive prenatal testing (NIPT) and non-invasive prenatal screening (e.g. for measuring fetal DNA fraction in maternal blood); evaluation or prediction of success of organ transplants (e.g. predicting rejection events by monitoring level of donor DNA in recipient's blood); evaluation of a sample to characterize DNA associated with cancers and DNA not associated with cancers (e.g., tumor DNA vs. non-tumor DNA); evaluation of a mixture of environmental samples (e.g., for detection of genetically modified organisms); forensic applications (e.g., detection of minute amounts of suspect DNA in a sample, which is difficult to detect by implementation of conventional PCR platforms); and other use cases.

In another specific use case, the systems, methods, and compositions of the disclosure can be used for evaluation of minimal residual disease (MRD) based upon detection of numbers of cancer cell targets present in a sample from a subject after one or more phases of cancer treatment (e.g., treatment of leukemia, treatment of lymphoma, treatment of multiple myeloma, etc.).

In another specific use case, the systems, methods, and compositions of the disclosure can be used for single nucleotide polymorphism genotyping (SNPtyping) to measure genetic variations of SNPs between members (e.g., members of a species). Additionally, the systems, methods, and compositions of the disclosure can be used for single nucleotide variant genotyping (SNVtyping) for germline DNA samples.

The systems, methods, and compositions of the disclosure can also be used for applications involving disease prediction generation and monitoring with multiplexed detection of markers of a gene expression marker panel (e.g., for pregnancy-associated complications, for other applications).

In another specific use case, systems, methods, and compositions described herein can be useful for ribosomal 16S and/or ITS characterization, where current sequencing technologies are fraught with high false positive rates and/or high PCR error. In relation to the specific use case, systems, methods, and compositions described can be used to disperse a sample of 16S and/or ITS ribosomal RNA (rRNA) across a plurality of partitions (as described in more detail below), where processing materials described enable detection of regions/sequences of interest (e.g., V3 region, V4 region, V5, region, other hypervariable regions, etc.), and subsequently, for operational taxonomic unit (OTU) or amplicon sequence variant (ASV) categorizations. For instance, detection of V3, V4, and/or V5 regions can be used for bacterial microbiome analyses, fungal microbiome analyses, other microbiome analyses, rare species detection, and/or other applications. Additionally or alternatively, such rRNA characterizations can be used for antimicrobial susceptibility testing (e.g., with a sample having one or more antibiotics being assessed, combined with bacteria and materials that can be used to indicate bacteria responses to the antibiotic(s)). Additionally or alternatively, such rRNA characterizations can be used for detection of a set of pathogens (e.g., up to 30 pathogens, up to 40 pathogens, up to 50 pathogens, up to 60 pathogens, up to 70 pathogens, etc.) and quantification (e.g., in relation to detection of presence or absence of various pathogens, in relation to characterization of infectious agents and potential prognoses). Additionally or alternatively, for microbial pathogen detection/quantification, any part of microbial genomics of a sample (e.g., non-rRNA targets) can be targeted, and subsequent detection can involve detection of sample composition (e.g., microbial composition, microbiome composition, etc.) without performance of next generation sequencing (NGS). In a related use case, detection/quantification of targets of a sample in a multiplexed manner can be used to differentiate between viral, fungal, and/or microbial infections (e.g., for a respiratory illness panel).

Additionally or alternatively, the systems, methods, and compositions of the disclosure can provide functionality for detection of other target analytes in a differentiable and multiplexed manner. In examples, analytes can include one or more of: DNA, RNA, miRNA, proteins, small molecules, single analytes, multianalytes, chemicals, and/or other analytes. For nucleic acid targets, capture probes of compositions described can include complementary molecules to the nucleic acid targets. For protein targets or small molecule targets, capture probes of the compositions described can include antibodies or aptamers conjugated with specific nucleic acid sequences for detection.

In another specific use case, the systems, methods, and compositions of the disclosure can provide functionality for detecting and quantifying a panel of synthetic targets, for instance, in order to provide quality controls for biological standards used to standardize assay performance with multiple synthetic targets in different concentrations. In another specific use case, nucleic acids exogenously introduced into cells (e.g., such as in genome editing applications, such as in CRISPR applications) can be measured using the systems, methods, and compositions of the disclosure described (e.g., for genome editing applications, for gene therapy applications).

The systems, methods, and compositions of the disclosure can be applied to samples from human organisms, other multicellular animals, plants, fungi, unicellular organisms, viruses, and/or other material, with respect to evaluating presence or absence of sets of targets in parallel. Characterizations of the sets of targets can then be used for diagnostic purposes and/or for generation of targeted therapies to improve states of organisms from which the samples were sourced. The systems, methods, and compositions of the disclosure can also provide value in research or other non-clinical settings, with or without evaluation and processing of live human or mammalian biological material, and without the immediate purpose of obtaining a diagnostic result of a disease or health condition.

In combination with a higher number of colors/dyes used for detection, the systems, methods, and compositions of the disclosure can further improve the number of targets that can be detected from a sample within a single container, in a single-tube workflow.

The systems, methods, and compositions of the disclosure can confer the benefit of providing non-naturally occurring compositions for facilitating interactions with and amplification of a large set of target analytes from a sample in parallel, with improved efficiency, without utilizing complex microfluidic setups, and in a manner that reduces overall costs. As such, the systems and methods of the present disclosure provide a cost-competitive alternative to other methods for detection and digital quantitation of a large number of target analytes in a multiplexed manner.

The systems, methods, and compositions of the disclosure can provide mechanisms for target-specific/allele-specific amplification and can be applied to digital polymerase chain reaction (dPCR) and/or other PCR-associated assays.

Additionally or alternatively, the systems, methods, and compositions of the disclosure can confer any other suitable benefit.

2. Methods and Materials

As shown in FIG. 1A, embodiments of a method 100 for multiplexed detection and quantitation of targets includes: detecting signals indicative of a profile of a set of targets, from a sample distributed across a set of partitions (e.g., a high number of partitions at low occupancy) S110, and returning a characterization of the sample based upon the profile S120. In embodiments, said signals correspond to a set of color combinatorics and/or other differentiable signals resulting from probes used to tag targets, wherein color combinatorics of the set of color combinatorics are paired with targets of the set of targets, and where the set of targets has a total number greater than the number of color channels used to detect colors corresponding to the set of color combinatorics. As such, the method can provide unique labeling for multiplexed characterization of a panel of targets based upon color combinatorics, without requiring traditional multiplexing based solely upon signal amplitudes.

In a variation, as shown in FIG. 113, a method 100b for characterization of non-self genetic material from a sample containing self genetic material and non-self genetic material can include: detecting signals indicative of a profile of a set of set of single nucleotide polymorphisms (SNPs) from a sample distributed across a set of partitions Snob, and returning a characterization of relative abundance of alleles of each SNP in the set of SNPs to generate an estimate of non-self-genetic material in the sample S120b.

Figure 1C:
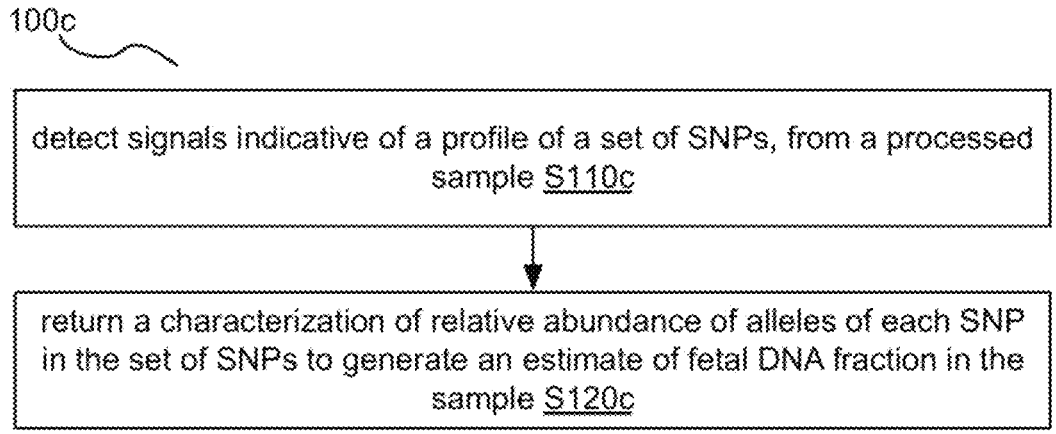
FIG. 1C depicts a flowchart of a variation of a method for multiplexed detection and digital quantitation of targets, with applications in characterizing fetal fraction in a sample.

In a specific example, as shown in FIG. 1C, a method 100c for determination of fetal fraction (FF) can include: detecting signals indicative of a profile of a set of SNPs from a sample distributed across a set of partitions S110c, and returning a characterization of relative abundance of alleles of each SNP in the set of SNPs to generate an estimate of fetal DNA fraction in the sample S120c.

Figure 1D:
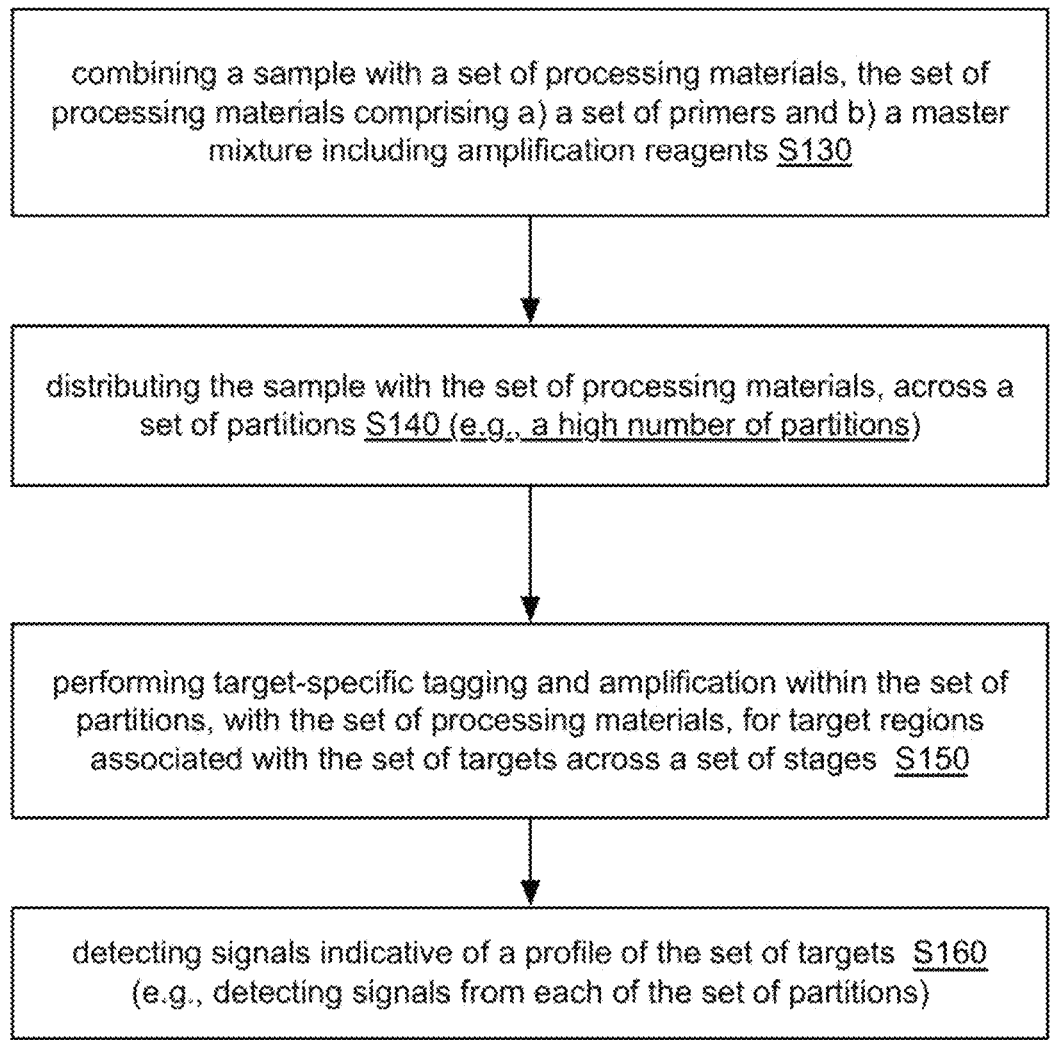
FIG. 1D depicts a flowchart of portions of an embodiment of a method for multiplexed detection and digital quantitation of targets.

One or more of the methods described can further include operations for processing a sample or providing an environment for producing the processed sample such that it can produce signals indicative of the profile(s), where processing the sample can include (as shown in FIG. 1D): combining a sample with a set of processing materials, the set of processing materials comprising a) a set of primers (e.g., for each of the set of targets, a set of target-specific forward primers corresponding to different targets of the set of targets, and a common reverse primer for the set of target-specific forward primers; other primer designs), and b) a master mixture including amplification reagents S130; distributing the sample with the set of processing materials, across a set of partitions (e.g., a high number of partitions at low occupancy, such that different targets of the set of targets do not co-inhabit a single partition) S140; performing target-specific (e.g., allele-specific) tagging and amplification, with the set of processing materials, for target regions associated with the set of targets across a set of stages S150; and detecting signals indicative of a profile of the set of targets S160.

The methods can enable detection of genetic variations in biological sample material, in a multiplexed manner. In more detail, the methods enable performance of ultra-high multiplexed target detection by implementing a high number of partitions (e.g., more than 100,000 partitions, more than 200,000 partitions, more than 500,000 partitions, more than 1 million partitions, more than 10 million partitions, more than 20 million partitions, more than 30 million partitions, more than 50 million partitions, more than 100 million partitions, etc.) with low-occupancy (e.g., less than 10% occupancy, less than 8% occupancy, less than 5% occupancy, etc.) of partitions by targets. In particular, use of a low-occupancy platform involving high numbers of partitions provides a regime where the probability of encountering more than one target in a partition is very low, such that a unique color combination can be inferred from the particular target color-coded by the unique color combination.

In relation to detection and effective use of sample processing materials, the systems and methods of the present disclosure involve detection of signals from targets of interest of a processed sample, where the signals correspond to different color combinatorics of a set of color combinatorics, alone or in combination with other types of differentiable signals, where color combinatorics of the set of color combinatorics are paired with targets of the set of targets, and where the set of targets has a total number greater than the number of color channels used to detect colors corresponding to the set of color combinatorics. In particular, due to the high-degree of partitioning described, any positive partition (e.g., droplet of an emulsion generated from the sample and containing a target) will contain only one color combination corresponding to fluorescent materials used during processing of the sample, thereby providing an accurate mechanism for multiplexed detection.

In specific examples, methods of the present disclosure can provide a multi-color combinatoric scheme with 5-color assay. As described in more detail below, the methods can provide mechanisms for multi-color combinatorics using competitive target-specific or allele-specific assays (e.g., Kompetitiv allele-specific PCR (KASP®), PCR allele competitive extension (PACE™), etc.) and/or other assay chemistries, because they involve no additional probe sequence within generated amplicons, provide a low degree of assay complexity, and thus result in significantly reduced assay cost for a panel of targets. In variations, such assays can be based upon target-specific (e.g., allele-specific) oligonucleotide extension and fluorescence resonance energy transfer for signal generation. In alternative variations, such assays can be based upon generation and detection of other types of signals.

The methods can further provide functionality for multiplexed detection of genetic variants in a sample by optimizing the amount of information obtained using lower-cost and/or a reduced set of sample processing materials compared to traditional assays based upon fluorescent detection, involving a higher number of primer types, probe types, quencher types, and probe additives. In combination with a higher number of colors/dyes used for detection, the methods can further improve the number of targets that can be detected from a sample within a single container.

The method(s) can be implemented by embodiments, variations, and examples of system components described in U.S. application Ser. No. 17/230,907 filed on 14 Apr. 2021 and/or U.S. application Ser. No. 17/687,080 filed 4 Mar. 2022, which are each hereby incorporated in its entirety by this reference. Additionally or alternatively, the method(s) can be implemented by other system elements.

Sample Types and Targets: In variations, the method 100 can be used to process sample types including biological fluids including or derived from one or more of: blood (e.g., whole blood, peripheral blood, non-peripheral blood, blood lysate, etc.), plasma, serum, saliva, reproductive fluids, mucus, pleural fluid, pericardial fluid, peritoneal fluid, amniotic fluids, otic fluid, sweat, interstitial fluid, synovial fluid, cerebral-spinal fluid, urine, gastric fluids, biological waste, other biological fluids; tissues (e.g., homogenized tissue samples); food samples; liquid consumable samples; and/or other sample materials. Samples can be derived from human organisms, other multicellular animals, plants, fungi, unicellular organisms, viruses, and/or other material. In specific examples, samples processed can include maternal samples (e.g., blood, plasma, serum, urine, chorionic villus, etc.) including maternal and fetal material (e.g., cellular material, cell-free nucleic acid material, other nucleic acid material, etc.) from which prenatal detection or diagnosis of genetic disorders (e.g., aneuploidies, genetically inherited diseases, other chromosomal issues, etc.) can be performed.

In embodiments, targets detected in a multiplexed manner according to embodiments, variations, and examples of the method 100 can include: nucleic acids (e.g., DNA, RNA, miRNA, etc.), proteins, amino acids, peptides, small molecules, single analytes, multianalytes, chemicals, and/or other target material, in order to enable genomic, proteomic, and/or other multi-omic characterizations and diagnoses for various applications. Genetic targets can include one or more of: single nucleotide polymorphisms (SNPs), copy number variations (CNVs), insertions, deletions, genes, methylated loci, and/or other loci of interest.

In variations, SNPs tagged in a massively parallel manner and detected in a multiplexed manner according to methods described can include SNPs associated with any chromosome having a minor allele fraction (MAF) greater than 0.4. SNPs evaluated can alternatively be characterized by MAF above another suitable threshold (e.g., MAF>0.2, MAF>0.3, etc.). SNPs evaluated can be for coding regions (e.g., synonymous, non-synonymous, missense, nonsense) and/or non-coding regions. SNPs evaluated can be biallelic or multiallelic, with more than two alleles per SNP.

In examples, SNPs can be associated with chromosomes 13, 18, 21, X, Y, and/or other chromosomes, at various loci (e.g., from 10 to 20,000 polymorphic loci); however, SNPs evaluated can additionally or alternatively be associated with other chromosomes and/or loci. Furthermore, the size of the panel of targets can be determined based upon the likelihood of detecting at least one SNP that is homozygous in the mother and heterozygous in the fetus, such that it can be used as a marker for estimation of FF.

The size of the SNP panel being evaluated, threshold MAF for each SNP, and chromosomal distribution can thus be selected to optimize or otherwise increase the probability of returning an accurate estimate of FF or other characterization, based upon the methods described.

Furthermore, SNPs selected for evaluation can have allele pairs that are well-discriminated (e.g., with respect to stabilizing-destabilizing characteristics). For instance, SNPs can be selected with prioritization of G/T, C/A, and T/A SNPs having high destabilization strength characteristics.

In examples, SNPs can include one or more of: rs2737653 with G/T alleles, rs2737654 with T/G alleles, rs1160680 with C/T alleles, rs701232 with C/T alleles, rs1736442 with A/G alleles, rs7232004 with G/T alleles, rs1498553 with C/T alleles, and other suitable SNPs.

Additionally or alternatively, in other specific applications, target material tagged in a multiplexed manner and evaluated according to methods described can provide diagnostics and/or characterizations in relation to one or more of: monitoring or detection of products (e.g., proteins, chemicals) released from single cells (e.g., interleukins or other compounds released from immune cells); monitoring cell survival and/or division for single cells; monitoring or detection of enzymatic reactions involving single cells; antibiotic resistance screening for bacteria; characterization of pathogens in a sample (e.g., in relation to infections, sepsis, in relation to environmental and food samples, etc.);

microbiome characterizations (e.g., based upon detection of hypervariable regions of rRNA); characterization of heterogeneous cell populations in a sample; characterization of individual cells or viral particles; monitoring of viral infections of a single host cell; liquid biopsies and companion diagnostics; detection of cancer forms from various biological samples (e.g., from cell-free nucleic acids, tissue biopsies, biological fluids, feces, etc.) based upon characterization of target panels; detection and/or monitoring of minimal residual diseases; monitoring responses to therapies; detection or prediction of rejection events of transplanted organs; other diagnostics associated with other health conditions; other characterizations of statuses of other organisms; and other suitable applications.

2.1 Method—Assay Materials and Compositions 2.1.1 Method—Assay Materials and Compositions for Competitive Target-Specific Assays Step S130 recites: combining the sample with a set of processing materials, which functions to tag and amplify multiple targets of the sample in parallel. The set of processing materials described here in Section 2.1.1 can include fewer components (e.g., requiring just forward and reverse primers, requiring single primers with tandem adapters, using shared probes/quencher oligonucleotides for primers targeting different targets, etc.) to provide detection of multiple targets in parallel. For instance, for a set of colors/wavelengths used for detection and digital quantitation of multiple targets based on color combinatorics, the set of processing materials can include only one probe for each of the set of colors/wavelengths, rather than one probe per target of interest. As such, probes can be designed against a common PCR adapter tagged to forward and/or reverse primers of the set of processing materials, where the number of probes used has a number corresponding to the number of channels for detection, rather than the number of targets, thereby significantly reducing assay cost. As such, the set of processing materials implements chemistry for differential discrimination of partition contents based on color combinatorics, where color combinatorics of a set of color combinatorics are paired with targets of a set of targets of interest, and where the set of targets has a total number greater than the number of color channels used to detect colors corresponding to the set of color combinatorics.

Figure 2:
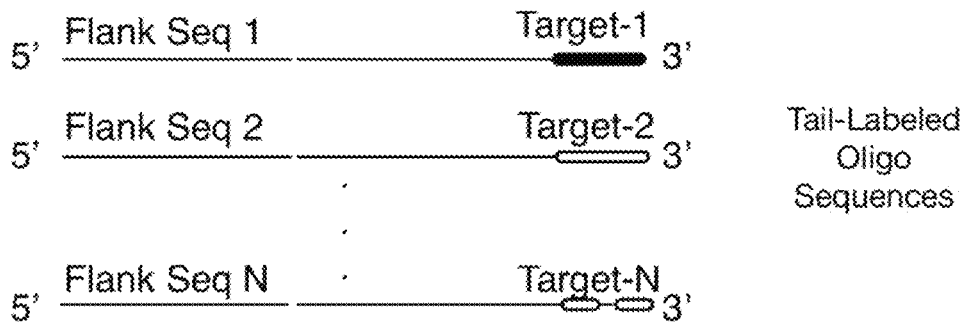
FIG. 2 depicts a schematic of components implemented in an embodiment of a method for multiplexed detection of targets.
Figure 2:
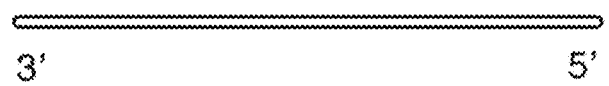
Figure 2:
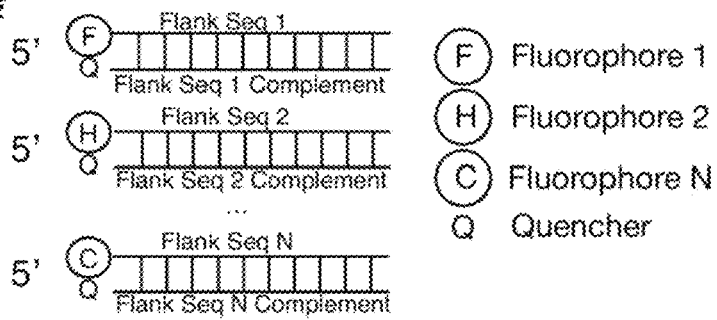
Figure 2:
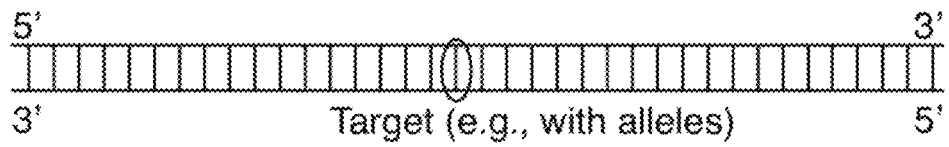

In embodiments, as shown in FIG. 2, the set of processing materials can include: a) for each of the set of targets, a set of target-specific (e.g., allele-specific) forward primers corresponding to different alleles of a respective target of the set of targets, and a common reverse primer for the set of target-specific (e.g., allele-specific) forward primers, and b) a master mixture including amplification reagent as well as: for each of the set of targets, a set of target-specific (e.g., allele-specific) flanking sequences corresponding to different targets of the set of targets.

For each target (e.g., SNP, CNV, loci of interest, insertion, deletion, other target) with allelic variations, the set of target-specific forward primers can include an allele-specific forward primer for each allele. As such, the set of target-specific forward primers can include two allele-specific forward primers, or greater than two allele-specific forward primers (e.g., 3 allele-specific forward primers, 4 allele-specific forward primers, 5 allele-specific forward primers, etc.) for multiallele variations. The allele-specific forward primers include sequence portions complementary to alleles of targets, such that the primer groups encode the target (e.g., SNP, other target) being evaluated, and colors/fluorophores detected provide indication of which allele of a target is present.

The allele-specific forward primers for each target are configured to be competing, and include unique tail sequences for each allele. In variations, the tail sequences include oligonucleotides with a label corresponding to a dye/fluorophore that can be detected after sample processing. The label can be positioned at the 5' end of the forward primer or the 3' end of the forward primer, or can otherwise be positioned (e.g., at a position intermediate the 3' and 5' ends). In variations, each forward primer can include multiple labels. The target-specific forward primers can incorporate mismatches at or near penultimate sites (e.g., depending upon destabilization effects of allele combinations associated with targets being evaluated). In variations, the common reverse primer can additionally or alternatively include one or more labels, and/or the set of processing materials can include multiple reverse primers.

Concentrations of forward primers can range from 50 nM to 300 nM in solution, or alternatively, less than 50 nM or greater than 300 nM in solution. Concentrations of reverse primers can range from 100 nM to 600 nM in solution, or alternatively, less than 100 nM or greater than 600 nM in solution. Concentrations of reporter oligonucleotides (e.g., fluorescent reporter oligonucleotides) can range from 30 nM to 200 nM in solution, or alternatively, less than 30 nM or greater than 200 nM in solution. Concentrations of quencher oligonucleotides can range from 100 nM to 600 nM in solution, or alternatively, less than 100 nM or greater than 600 nM in solution.

Primers (e.g., forward primers, reverse primers) can have lengths of 20 base pairs, 21 base pairs, 22 base pairs, 23 base pairs, 24 base pairs, 25 base pairs, 26 base pairs, 27 base pairs, 28 base pairs, 29 base pairs, 30 base pairs, 35 base pairs, 40 base pairs, 45 base pairs, 50 base pairs, an intermediate number of base pairs, or a greater number of base pairs. In variations, primers can incorporate sequence regions corresponding to probes and target sequences (e.g., a 20 base pair target sequence, a target sequence having another suitable length, etc.), and be designed for various levels of plexy (e.g., 1-plex conditions, 2-plex conditions, 3-plex conditions, 4-plex conditions, 5-plex conditions, 6-plex conditions, 7-plex conditions, etc.) as described. In variations, forward primers can be longer than reverse primers, and in specific examples, used of forward primers having lengths 5-10 base pairs longer (e.g., than reverse primers, than another reference length) produced higher counts (e.g., 8-10% higher counts) and higher SNR values (e.g., 12-17% higher SNR values) in relation to shorter primer lengths, when detecting of targets from partitions, thereby providing higher detection performance.

Primers (e.g., forward primers, reverse primers) can have annealing temperatures from 48 C-65 C or another suitable annealing temperature range based upon reactions performed according to various assays. Primers (e.g., forward primers, reverse primers) can have melting temperatures from 65 C to 70 C (e.g., from 67 C to 68.8 C) or another suitable melting temperature range based upon reactions performed according to various assays.

Characteristics of forward and reverse primers described above can be reversed (e.g., the set of processing materials can include a forward primer and a set of target-specific reverse primers). Still alternatively, both forward and reverse primers can be target-specific.

As noted briefly above and shown in FIG. 2, in embodiments, the master mixture can include amplification reagents and, for each of the set of targets, a set of target-specific flanking sequences corresponding to different targets of the set of targets, in order to support multiplexed processing, detection, and digital quantitation. As such, in one variation, the set of processing materials can include, for a target of the set of targets: a primer set comprising: a common primer and a set of target-specific primers structured to interact with a target region of the target, the set of target-specific primers comprising a first target-specific primer comprising a first flanking sequence, and a first fluorophore-labeled oligonucleotide corresponding to the flanking sequence, the first fluorophore-labeled oligonucleotide comprising a first fluorophore configured to transmit a first target signal if the target region is amplified.

For tagging a target with probes configured to emit multiple colors (where tandem probes are described in more detail below), the set of target-specific primers can further include a second target-specific primer comprising a second flanking sequence, and the set of processing materials further comprises a second fluorophore-labeled oligonucleotide corresponding to the second flanking sequence, the second fluorophore-labeled oligonucleotide comprising a second fluorophore configured to transmit a second target signal if the target region is amplified, such that the target can be positively detected based upon the first target signal and the second target signal. Alternatively, a single primer can be used to tag the target, along with tandem adapters corresponding to the probes used to tag the targets. As such, the set of processing materials can include at least one primer structured to tag the target with a first probe having a first fluorophore and a second probe having a second fluorophore (and/or additional probes with additional fluorophores), wherein the first fluorophore and the second fluorophore (and optional additional fluorophores) correspond to two (or more) color channels of the number of color channels.

The master mixture can include a probe including a dye/fluorophore with complementary quencher for each target, a polymerase (e.g., Taq polymerase), dNPTs, and buffer components.

With respect to tagging implemented using the forward primers, and corresponding dyes/fluorophore families of probes, dyes/fluorophores can be associated with chemical families including: acridine derivatives, arylmethine derivatives, fluorescein derivatives, anthracene derivatives, tetrapyrrole derivatives, xanthene derivatives, oxazine derivatives, dipyrromethene derivatives, cyanine derivatives, squaraine derivates, squaraine rotaxane derivatives, naphthalene derivatives, coumarin derivatives, oxadiazole derivatives, pyrene derivatives, and/or other chemicals. Such fluorophores can further be attached to other functional groups as needed for tagging of targets in a detectable manner.

In examples, dyes (e.g., for tagging of RNAs, DNAs, oligonucleotides, etc.) can include one or more of: FAM, (e.g., 6-FAM), Cy3™, Cy5™, Cy5.5™, TAMRA™ (e.g., 5-TAMRA, 6-TAMRA, etc.), MAX, JOE, TET™, ROX, TYE™ (e.g., TYE563, TYE 665, TYE 705, etc.), Yakima Yellow®, HEX, TEX (e.g., TEX 615), SUN, ATTO™ (e.g., ATTO 488, ATTO 532, ATTO 550, ATTO 565, ATTO Rho101, ATTO 590, ATTO 633, ATTO 647, etc.), Alexa Fluor® (e.g., Alexa Fluor 488, Alexa Fluor 532, Alexa Fluor 546, Alexa Fluor 594, Alexa Fluor 647, Alexa Fluor 660, Alexa Fluor 750, etc.), IRDyes® (e.g., 5'IRDye 700, 5'IRDye Boo, 5'IRDye 800CW, etc.), Rhodamine (e.g., Rhodamine Green, Rhodamine Red, Texas Red®, Lightcycler®, Dy 750, Hoechst dyes, DAPI dyes, SYTOX dyes, chromomycin dyes, mithramycin dyes, YOYO dyes, ethidium bromide dyes, acridine orange dyes, TOTO dytes, thiazole dyzes, CyTRAK dyes, propidium iodide dyes, LDS dyes, BODIPY dyes, and/or other dyes.

In examples, cell function dyes for tagging of target material and detection can include one or more of: DCFH, DHR, SNARF, indo-1, Fluo-3, Fluo-4, and/or other dyes.

In examples, fluorescent proteins for tagging of target material and detection can include one or more of: cerulean, mCFP, mTurquoise, T-Sapphire, CyPet, ECFP, CFP, EBFP, Azurite, and/or other fluorescent proteins.

Dyes/fluorophores implemented can correspond to wavelength ranges in the visible spectrum and/or non-visible spectrum of electromagnetic radiation. Furthermore, dyes/fluorophores implemented can be configured to prevent overlapping wavelengths (e.g., of emission) and/or signal bleed through with respect to multiplexed detection and achieving high SNR values involving detection of signals from packed partitions. In variations, the set of processing materials can include components for 7 wavelength ranges for multiplexed detection of targets; however, the set of processing materials can include components for less than 7 wavelength ranges (e.g., one wavelength, two wavelengths, three wavelengths, four wavelengths, five wavelengths) or more than 7 wavelength ranges.

Quencher oligonucleotides implemented can include a quencher molecule configured such that, when the quencher oligonucleotide anneals with a primer having a fluorophore, the quencher molecule is in proximity to (e.g., directly opposite) the fluorophore in order to quench the fluorophore. Additionally or alternatively, quenchers can include one or more of: black hole quenchers, static quenchers, self-quenchers (e.g., fluorophores that self-quench under certain conditions by producing secondary structures or other structures), and/or other suitable quenchers. Variations of positions of quenchers (e.g., when tandem probes are involved) are described in more detail below.

The set of processing materials of Step S130 can additionally or alternatively include implementation of components structured to improve signal-to-noise ratio (SNR) characteristics in the context of multiplexed detection, by increasing signal characteristics and/or reducing background (e.g., noise other artifacts). The components can include one additive for each wavelength range/color for detection (as opposed to one additive for each target/SNP being evaluated). Additionally or alternatively, the additives can have from 5-20 bases or another suitable number of bases. Additionally or alternatively, modified nucleic acids (e.g., such as locked nucleic acids (LNA) or other modified nucleic acids) can be incorporated into forward and/or reverse primers of the set of processing materials to improve SNR. In variations, LNA content can occupy a percentage (e.g., 10-60% LNA content) of the respective primer to improve SNR, where LNA content can be biased toward the 3' end, the 5' end, or intermediate the 3' and 5' ends.

However, the set of processing materials can additionally or alternatively include other suitable components and/or be configured in another suitable manner.

Furthermore, with respect to different wavelength ranges, different targets can be tagged with dye/fluorophore colors in a manner that promotes discrimination of results (e.g., without overlap) upon detection of signals from processed sample material. Furthermore, different targets can be matched with different combinations of colors/associated wavelengths in order to provide distinction upon detection of signals from processed sample materials. Variations and examples of multiplexing based upon color combinatorics and other features are provided below.

2.1.2 Multiplexing Based Upon Color Combinatorics

In relation to Step S130, the method can include: detecting signals from the set of partitions (e.g., droplets of an emulsion), wherein the signals correspond to a set of color combinatorics paired with targets of a set of targets potentially represented in the sample and contained within partitions of the set of partitions, and wherein the set of targets has a total number greater than the number of color channels used to detect colors corresponding to the set of color combinatorics S132. In variations, the set of color combinatorics involves combinations of up to 3 colors detectable from each of the set of partitions, up to 4 colors detectable from each of the set of partitions, up to 5 colors detectable from each of the set of partitions, up to 6 colors detectable from each of the set of partitions, up to 7 colors detectable from each of the set of partitions, up to 8 colors detectable from each of the set of partitions, or another suitable number of colors detectable from each of the set of partitions.

Figure 3A:
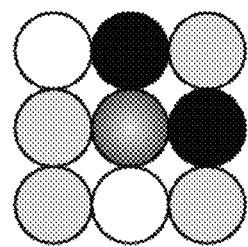
FIG. 3A depicts a schematic of differences in multiplexing with low-partition systems in comparison to high-partition systems.
Figure 3A:
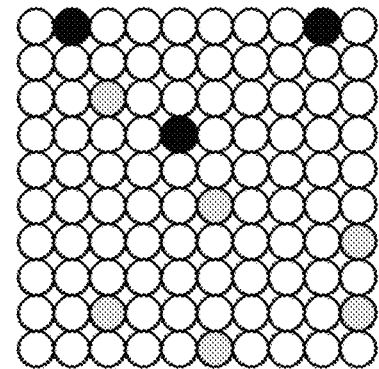
Figure 3A:
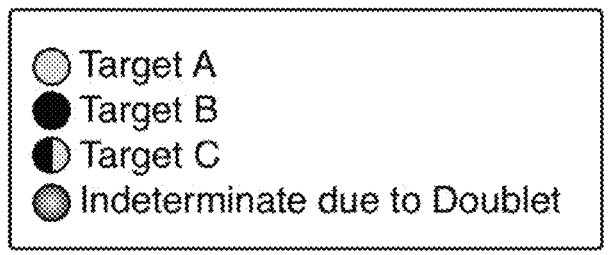
Figure 3A:
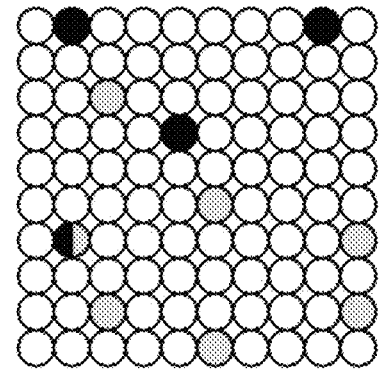

Multiplexing with color combinatorics is practically achievable using embodiments of the systems, methods, and processing materials described, especially due to the large number of partitions available (as described), and in some instances, low occupancy of partitions by targets (as described). For instance, as shown in FIG. 3A (left), low-partition systems are subject to greater prevalence of multiple targets within a single partition (e.g., as in doublets, as in triplets), thereby contributing to a lower degree of multiplexed assay sensitivity. However, high-partition systems, also shown in FIG. 3A (right) are subject to lower prevalence of multiple targets within a single partition (e.g., as in doublets, as in triplets), thereby contributing to a higher degree of multiplexed assay sensitivity when color combinatorics are used. As such, a higher percentage of different targets that are tagged with combinations of colors can be accurately discriminated with the high partition platform described. Table 1 below provides example scenarios indicating doublet rates observable for systems with 20,000 partitions and 30,000,000 partitions (as in system embodiments described), respectively, where doublet rates are provided for various inputs/counts per color channel used for scanning (and a significantly lower percentage of doubles are observed with a high number of partitions).

TABLE 1

| Inputs/Counts per channel | 20K Partitions | 30M Partitions |
|---|---|---|
| | Doublet rate | |
| 1000 | 4.877% | 0.003% |
| 5000 | 22.120% | 0.017% |
| 10000 | 39.347% | 0.033% |
| 50000 | 91.792% | 0.167% |
| 100000 | 99.326% | 0.333% |
| 1000000 | — | 3.278% |

Furthermore, when implementing four or more colors for tagging a set of targets for multiplexed detection, the method 100 can include tagging targets with combinations of three or more colors, in order to reduce or otherwise eliminate error due to presence of doublets (i.e., two targets within a partition), where doublet targets, each tagged with single colors, would result in dual color partitions. Similarly, the method 100 can include tagging targets with combinations of four or more colors, in order to reduce or otherwise eliminate error due to presence of triplets (i.e., three targets within a partition), where triplet targets, each tagged with single colors, would result in tricolor partitions.

Figure 3B:
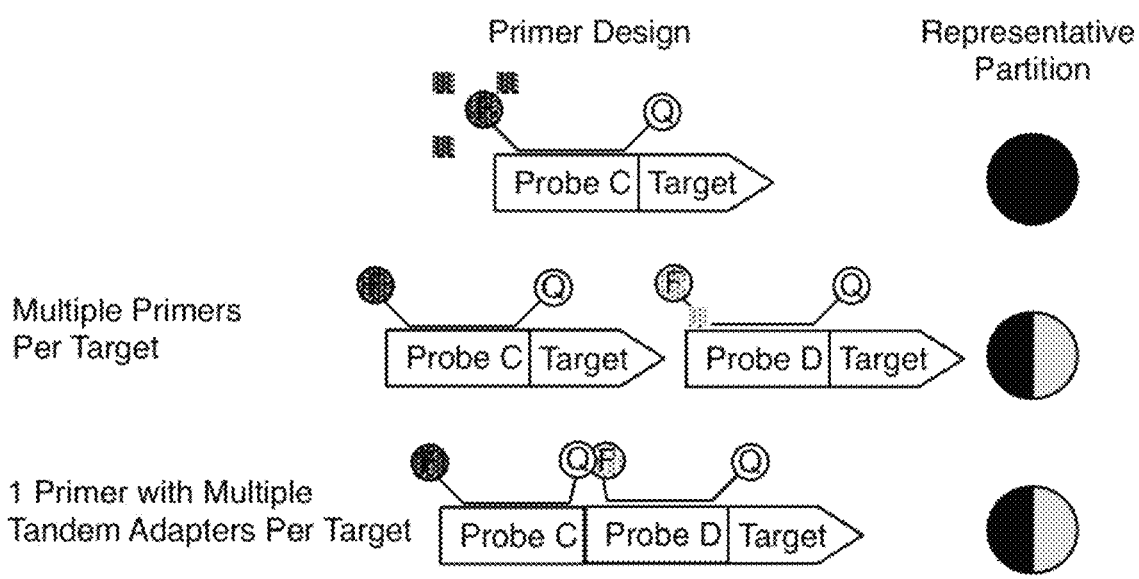
FIG. 3B depicts a schematic of different strategies for labeling a target with one or more probes in accordance with embodiments of the disclosure.

In relation to the set of processing materials described, labeling a target with multiple colors can be performed using multiple primers per target (e.g., gene), where each of a set of primers (e.g., forward primers) used to tag a respective target can tag the respective target with one of a set of dyes/fluorophores (2 primers/tandem probes are shown in representative FIG. 3B, but the methods can be adapted to more than 2 primers/tandem probes). Alternatively, labeling a target with multiple colors can be performed using a single primer (e.g., forward primer) for the target, along with tandem adapters (shown in FIG. 3B), where tandem adapters and probes are described in more detail in Section 2.1.3 below. Different tagging strategies (e.g., multiple primers per target vs. single primer per target) can be implemented. For instance, a set of primers (e.g., forward primers) can be used for tagging a first target with multiple colors, and a single primer (e.g., forward primer) can be used for tagging a second target with one or more colors. When using multiple primers, in silico primer design can be used to prevent undesired primer-primer, primer-probe, primer-amplicon (non-target) interactions and/or self-primer interactions (e.g., undesired hairpin structures, primer-dimer interactions, etc.) that could produce increased background during scanning.

In one example case, in silico primer design can include generating multiple pairs of primers for individual targets of interest, with check steps to remove candidates with potential for amplicon/primer/probe interactions, to remove primers with multiple continuous matches (e.g., 11 or more continuous matches) to reduce cross-channel interactions in signal positive droplets and primer-probe interactions or background noise before amplification. Primer sets can be selected from the best primer pairs for each target, with secondary check steps for undesired primer-primer interactions and primer-amplicon interactions, removal of primers with multiple base pair (bp) continuous matches or 9 bp continuous matches in a region (e.g., last 10 bases). Such design steps can be used to create primer sets for which background is reduced for every partition (during use), and for which cross-channel interactions in positive droplets are reduced. A resulting output of the in silico primer design operation produces a panel of compatible primers (e.g., with one primer pair per target of interest) for a specific multiplexing assay.

In relation to multiplexing with color combinatorics, labeling a target with multiple colors can be performed with combinations of colors, where the order of the colors used to tag a target is unaccounted for. Alternatively, labeling a target with multiple colors can be performed with permutations of colors, where the order of the colors used to tag a target is accounted for in relation to discrimination of a target. Permutation-based multiplexing is achievable using tandem probes used to tag targets, where tandem probes are described in more detail in Section 2.1.3 below. Implementation of fluorophores having transitionable fluorophore states (e.g., in response to a stimulus, in relation to exhibition of Foerster resonance energy transfer behavior, etc.) can also be used to achieve higher degrees of multiplexing, as described in more detail in Sections 2.1.3 and 2.1.4 below.

Figure 3D:
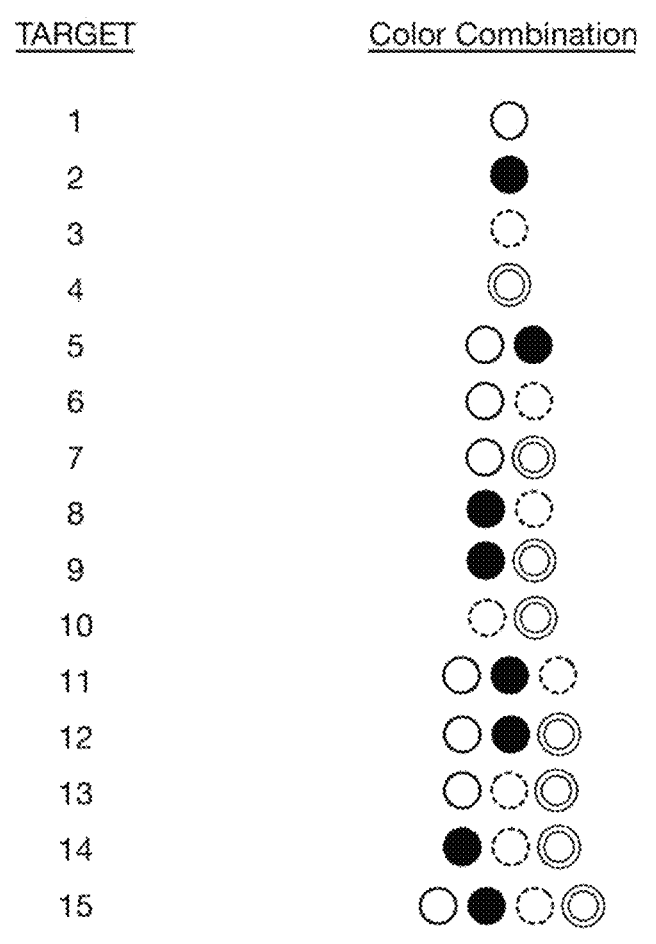

An example of targets (e.g., SNPs), corresponding alleles, and corresponding tagged-color combinations for detection and differentiation is shown in FIG. 3C, which enables encoding of 26 targets (e.g., 13 SNP loci) with a 5-color system (such that each partition can exhibit a color combinatoric of up to 5 colors). An example of targets (e.g., SNPs) and corresponding tagged-color combinations for detection and differentiation is shown in FIG. 3D, which enables encoding of 15 targets with a 4-color system (such that each partition can exhibit a color combinatoric of up to 4 colors). The example shown in FIGS. 3C and 3D can be adapted for systems greater than 5 colors or less than 4 colors. As such, with the ultra-high partition setting described involving limited dilution, each target of interest can be confidently labeled with a unique set of colors, for subsequent detection and digital quantitation without requiring multiplexing based upon signal amplitudes.

Assays can be designed such that targets are differentially tagged with combinations of colors in a manner that improves ability to discriminate color signals upon scanning and/or to use probes in a conservative and efficient manner. For instance, targets that are anticipated to be most prevalent can be tagged with fewer colors, and targets that are anticipated to be least prevalent can be tagged with more colors. Additionally or alternatively, non-similar targets (e.g., a first target and a second target that is non-similar to the first target) can be tagged with opposite color combinations, in order to improve the ability to discriminate non-similar targets upon scanning. For instance, in the context of microbiome analyses, bacteria-derived targets can be tagged with a first combination of colors and fungal targets can be tagged with a second combination of colors (e.g., colors that are complementary to the first combination of colors, colors that are near complementary to the first combination of colors, etc.) that allows for improved discrimination of bacterial targets and fungal targets upon scanning.

However, assay designs involving multiplexing with color combinatorics can be applied in another suitable manner.

2.1.3 Multiplexing with Tandem Probes, Conjugated Polymers, and Foerster Resonance Energy Transfer (FRET)

Figure 3E:
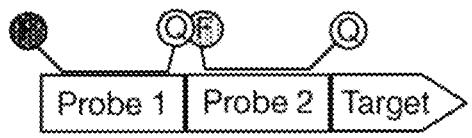
FIG. 3E depicts a schematic of an emulsion where targets within partitions are tagged in a manner involving color combinatorics in accordance with embodiments of the disclosure.
Figure 3E:
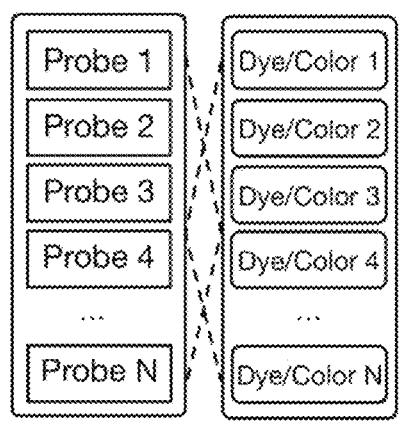
Figure 3E:
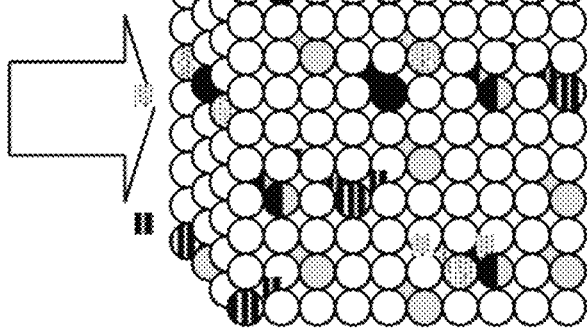

As noted above, higher degrees of multiplexing for partition-based systems can be achieved using tandem probes (e.g., a set of probes structured to tag the same target, for instance, with a single primer and tandem adapters for the target), such that each target being analyzed can be tagged with one or more of a set of probes (i.e., different probes configured to produce different color combinations of detectable signals). An example of a tandem probe design in shown in FIG. 3E, where individual probe sequences can be conjugated with one of a set of fluorophore/quencher combinations, and tagging a target with a subset of probes produces a signals that that can be detected with color channels appropriate to the subset of probes. As such, a target can be positively detected if signals corresponding to the subset of probes are detected from a partition upon scanning the set of partitions with color channels corresponding to the subset of probes.

Figure 3F:
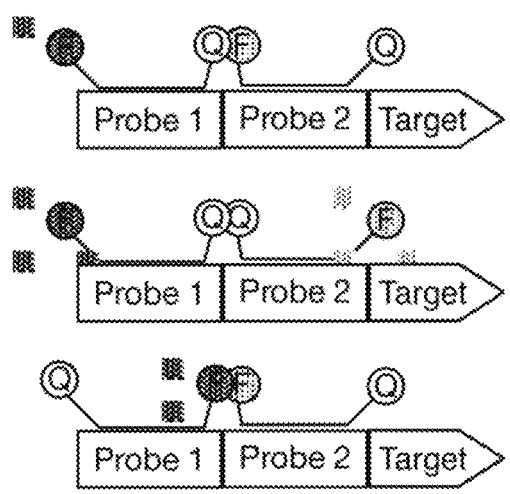
FIG. 3F depicts variations of tagging a target with tandem probes, in relation to positioning of fluorophores and quenchers.

In variations, the fluorophores of the set of probes can all be positioned near a first end (e.g., 3' end, 5' end) of the respective probe, and the quenchers of the set of probes can all be positioned near a second end (e.g., 5' end, 3' end) of the respective probe, such that, as shown in FIG. 3F (top), the quencher of a first probe is positioned near the fluorophore of a second probe when the first probe and the second probe have tagged a target in tandem. Alternatively, as shown in FIG. 3F (middle), a first probe and a second probe to be used for tagging of a target in tandem can be configured such that the quencher of the first probe and the quencher of the second probe are positioned near each other when the first probe and the second probe have tagged a target in tandem. Alternatively, as shown in FIG. 3F (bottom), a first probe and a second probe to be used for tagging of a target in tandem can be configured such that the quencher of the first probe and the quencher of the second probe are positioned far from each other when the first probe and the second probe have tagged a target in tandem. However, in variations, the fluorophores and/or quenchers of probes can be positioned away from ends (e.g., 3' ends, 5' ends) of respective probes. Fluorophore and quencher positions along the lengths of respective probes can thus be configured to improve signal detection (e.g., in relation to detection of fluorescent signals from partitions/emulsion droplets, with desired quenching performance (e.g., with respect to quencher interference or quencher enhancement within a partition) and with desired background reduction performance).

While only two tandem primers/tandem probes are shown in FIGURES, methods can be adapted and expanded to incorporate more than two primers/probes for target tagging. In particular, the methods described can involve up to 2 tandem probes for target tagging, up to 3 tandem probes for target tagging, up to 4 tandem probes for target tagging, up to 5 tandem probes for target tagging, up to 6 tandem probes for target tagging, up to 7 tandem probes for target tagging, up to 8 tandem probes for target tagging, up to 9 tandem probes for target tagging, up to 10 tandem probes for target tagging, or greater numbers of tandem probes for target tagging.

Additionally or alternatively, when the fluorophores of the set of probes can are positioned near a first end (e.g., 3' end, 5' end) of the respective probe, and the quenchers of the set of probes can all be positioned near a second end (e.g., 5' end, 3' end) of the respective probe, ordered positioning of a first probe with a first fluorophore and a first quencher and a second probe with a second fluorophore and a second quencher can be used to create different permutations of ordered probes that result in amplitude differentiation of signals for target detection. In particular, the effect of positioning quenchers and fluorophores in tandem and resulting signal intensity changes based upon positioning is due to FRET behavior, where, as a quencher of one probe is placed next to a fluorophore of another probe, the intensity of the fluorophore is reduced. Thus, by modulating relative positioning of quenchers and fluorophores of different probes used to tag a target, differential signal amplitudes for respective probes involved can be achieved and detected.

Figure 3G:
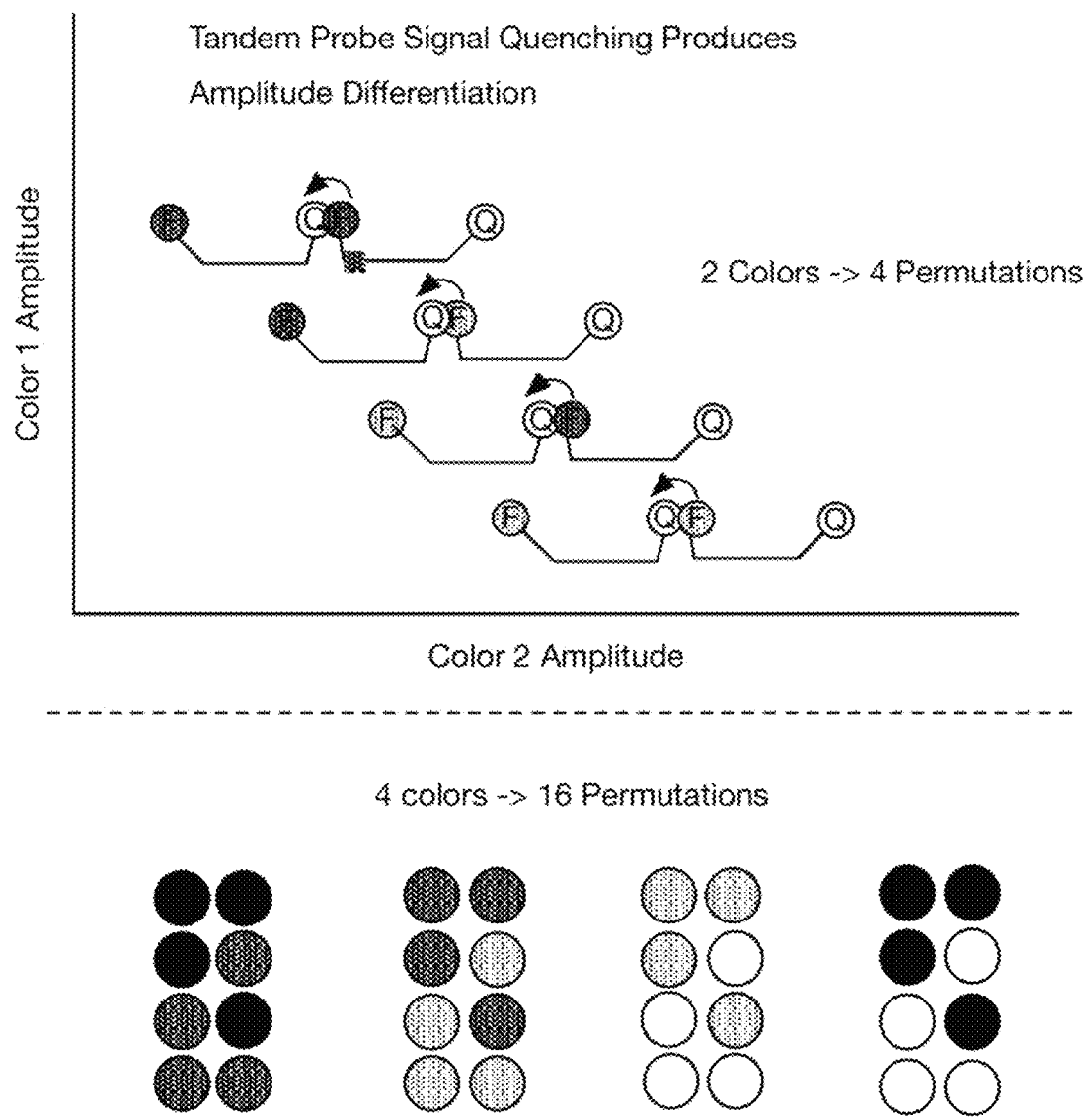
FIG. 3G depicts scenarios involving use of tandem probes and amplitude-based differentiation of signals involving two colors in accordance with embodiments of the disclosure.

In the examples shown in FIG. 3G, when two fluorophore colors (i.e., a first color and a second color) are available, tagging a target in tandem with a first probe having a first color and a second probe having the first color (FIG. 3G, top), enables detection of the target with a high amplitude signal corresponding to the first color. Tagging a target in tandem with a first probe having a first color and a second probe having a second color (FIG. 3G, second from top), enables detection of the target with a medium-high amplitude signal corresponding to the first color and a medium-low amplitude signal corresponding to the second color. Tagging a target in tandem with a first probe having a second color and a second probe having a first color (FIG. 3G, third from top), enables detection of the target with a medium-high amplitude signal corresponding to the second color and a medium-low amplitude signal corresponding to the first color. Tagging a target in tandem with a first probe having a second color and a second probe having a second color (FIG. 3G, bottom), enables detection of the target with a high amplitude signal corresponding to the second color. As such, when two colors are available, 4 permutations of ordered pairs of tandem probes are available for differential target tagging (with detectable signals based upon signal amplitude in different color channels corresponding to the colors available). When four colors are available, 16 permutations of ordered pairs of tandem probes are available (e.g., 4 permutations for each pair of colors), for differential target tagging, if only two probes are used per template. When four colors are available, 256 permutations are available (i.e., 4 probes with 4 colors×4 probes with 4 colors). Examples of signal amplitudes, for a scenario where four colors are available and pairs of tandem probes are used to tag targets, are shown in FIG. 3G. Variations of the examples shown in FIG. 3G may not have the fluorophores and quenchers positioned at opposite ends of their respective probe, to provide differentiation of signals from targets using such tandem probes.

Additionally or alternatively, a first quencher can be added to a first probe used to tag a target, and based on the position of the first quencher of the first probe, the amplitude of a signal produced by a second fluorophore of a second probe used to tag a target in tandem with the first probe is reduced during detection. The amplitude reduction of the second fluorophore of the second probe can then enable discernment of the order of which the first probe (with the first fluorophore) and the second probe (with the second fluorophore) are placed.

Additionally or alternatively, tandem probes can be configured to have a spacer region positioned between different probes used to tag the same target. The spacer region can reduce quenching effects provided by a quencher of a first probe and a fluorophore of a second probe positioned next to the first probe, where the length of the spacer modulates the quenching effect. As such, a longer spacer increases the resultant signal amplitude of a second probe spaced from the first probe by the spacer. Furthermore, resulting amplitudes associated with probes used can be modulated by tuning spacer length, in order to achieve additional granularity of amplitude levels of each dye used to tag one or more targets (and thus more permutations for multiplexing of targets). In variations, the spacer can have a length from 1 to 25 base pairs, and have a specific sequence or a random sequence, in relation to primer aspects described above.

Figure 3H:
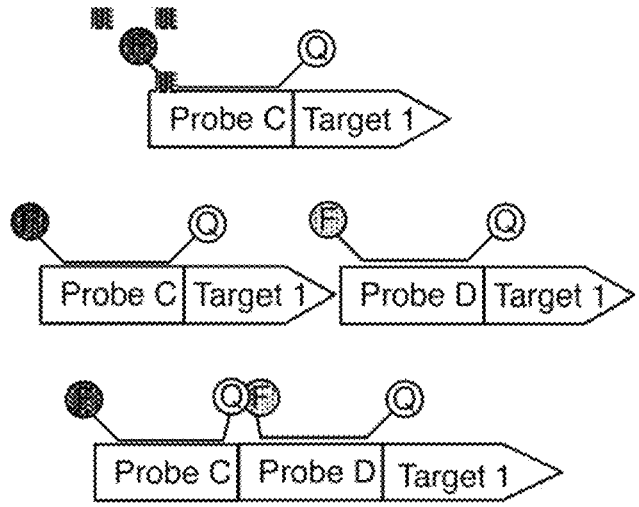
FIG. 3H depicts variations of tagging different targets of a sample with single probes or tandem probes.
Figure 3H:
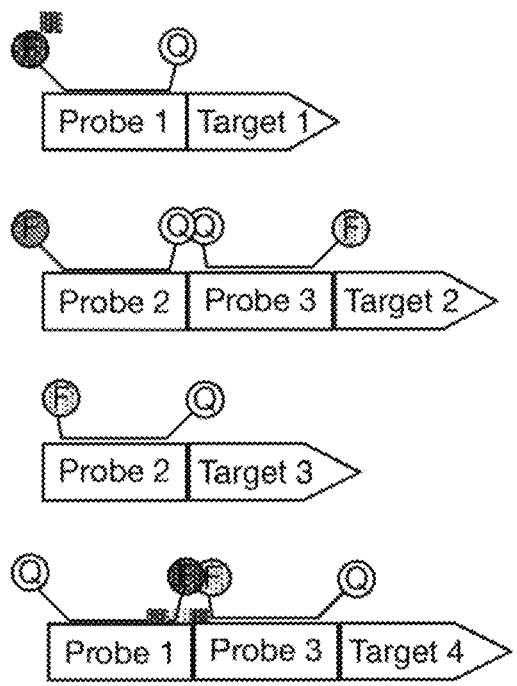

In variations, as shown in FIG. 3H (left), a target (e.g., target gene) can be tagged using a target-specific primer (e.g., forward primer) with one or more detectable probes (e.g., Probe C and/or Probe D shown in FIG. 3H). As shown in FIG. 3H (right), multiple targets (e.g., target genes) can be tagged using primers (e.g., forward primers) with single probes and/or combinations of tandem probes, with signal detection for target identification from partitions performed as described. As such, tandem primer/probes and non-tandem primer/probes can be combined within the set of processing materials for tagging of different targets.

Figure 3I:
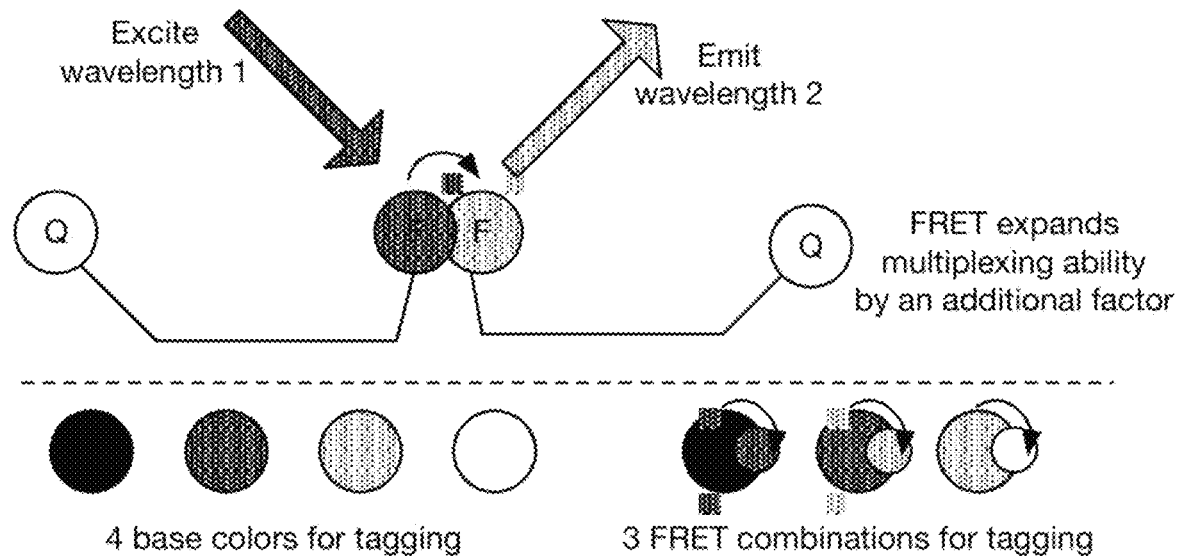
FIG. 3I depicts a variation of multiplexing involving probes capable of FRET behavior.

Alternatively, tandem probes where fluorophores are positioned near each other (as shown in FIG. 3I) and capable of producing and/or responding a Foerster resonance energy transfer (FRET) effect (e.g., with one or more emitting fluorophores and one or more reporting fluorophores) can be used to enable signal detection based on FRET behavior. For instance, a first probe of a tandem probe can be excited by a first wavelength of light that matches the excitation spectrum of the first fluorophore, and FRET transfer to a reporter dye of a second probe can excite the second probe for detection of a target (e.g., using emission filter specific for the emission spectrum of the second fluorophore), thereby enabling differential detection of targets from different partitions given that the excitation wavelength profiles and the emission wavelength profiles for the set of partitions is identifiable with scanning. As such, in relation to a first fluorophore and a second fluorophore included in processing materials as described, embodiments of the method can further include causing Foerster resonance energy transfer (FRET) from the first fluorophore to the second fluorophore upon exciting the first fluorophore with a first wavelength profile of light, such that detecting signals from the set of partitions with the number of color channels can include detecting the target from a partition upon scanning the set of partitions with a second wavelength profile of light corresponding to the second fluorophore. As shown in FIG. 3I, for an example set of four fluorophores that exhibit FRET behavior in tandem with excitation of a cooler color first probe and FRET transfer and detection of a warmer color second probe, differential tagging and detection can be achieved for 7 targets.

Figure 3J:
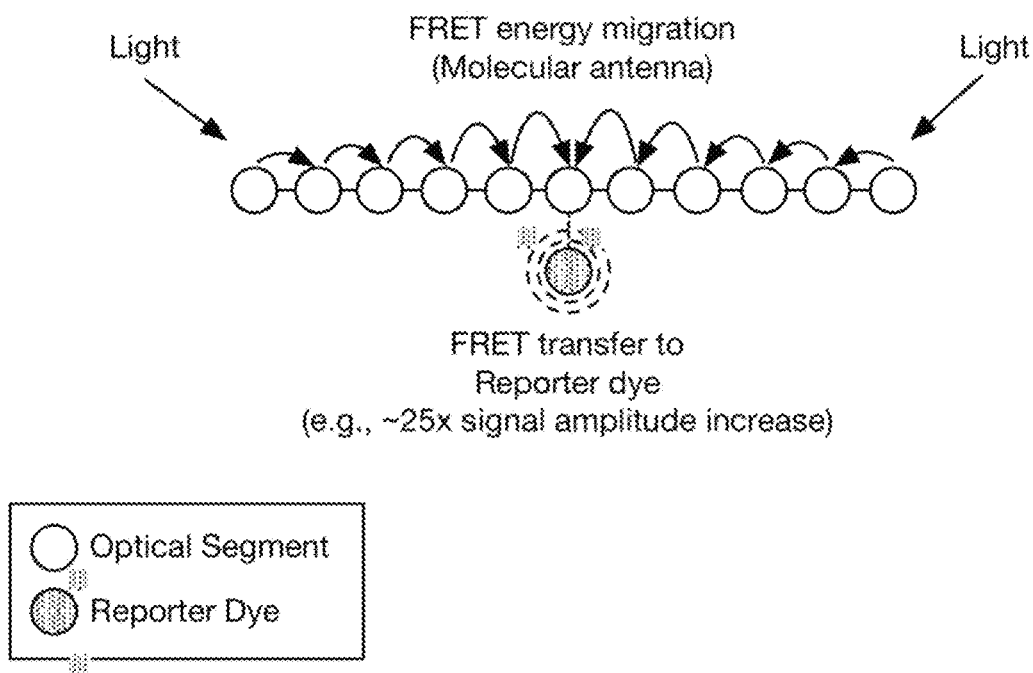
FIG. 3J depicts a schematic of an example of a FRET-capable probe.

As shown in FIG. 3J, the set of processing materials can additionally or alternatively include conjugated polymer probes for fluorescence enhancement, where such conjugated polymers operate as optical harvesters that exhibit long-range FRET capability. In more detail, as shown in FIG. 3J, a variation of a conjugated polymer probe includes a set of optical segments that harvest incident light with a large absorption cross-section. The structure of the conjugated polymer and set of optical segments determines the excitation wavelength. The set of optical segments operates as a molecular antenna and drive energy migration to a reporter dye of the probe, thereby achieving FRET transfer to the reporter dye.

Additionally or alternatively, conjugated polymer probes can include cationic polymers with complex structures (e.g., kinked structures, twisted structures, coiled structures, zig-zagging structures, etc.) capable of FRET transfer from such complex structures to a reporter dye for amplification of signals produced by the reporter dye, with or without an emission spectrum shift by the reporter dye. As such, a limited number of excitation spectra (e.g., associated with a limited number of color channels) can be used to achieve color detection across more colors than the limited number of color channels. Examples dyes that are included with or otherwise compatible with conjugated polymer probes include, for example, BD Horizon™ BB515, Alexa Fluor™ 488, FITC, BD Horizon™ BB630-P2, BD Horizon™ BB660-P2, PerCP-Cy5.5, PerC, BD Horizon™ BB700, BD Horizon™ BB755-P, BD Horizon™ BB790-P, and other BD Horizon™ components. Implementation of such conjugated polymer probes can, in some cases, be used to achieve detection of targets within partitions, with 12-color multiplexing, using only 2 colors of light sources.

Additionally or alternatively, conjugated polymer probes can form complexes (e.g., electrostatic complexes) with quantum dots or other structures in a manner that can produce a cascading FRET effect, whereby energy is transferred to the quantum dots or other structures, from the conjugated polymer structure(s), upon being subject to excitation wavelengths of light, and energy is transferred from the quantum dots or other structures to the dye of the probe, in order to produce higher sensitivity.

Reporter dyes can include dyes discussed above and/or other dyes with distinct emission behavior, where FRET-based amplification of dyes can result in an orders of magnitude (e.g., one order of magnitude, two orders of magnitude, three orders of magnitude, etc.) or greater amplification effect in comparison to dyes without a conjugated polymer component.

2.1.4 Multiplexing Based Upon Stimulus-Responsive Dyes and Fluorophores

Additionally or alternatively, in the context of partitions that are fixed in position or otherwise addressable (e.g., with barcoding, with identification of relative positions of partitions) across a set of scanning runs with the same color channel or different color channels, the method 100 can further include implementing stimulus-responsive dyes and/or fluorophores for tagging of targets, where scanning the set of partitions before and after applying a stimulus to the stimulus-responsive dyes and/or fluorophores enables additional levels of multiplexing to be achieved when using a limited number of color channels. As such, in relation to a base level of multiplexing achievable for a set of available color channels, the level of multiplexing can be expanded beyond the base level by a factor corresponding to the number of stimulus-responsive states available for each dye/fluorophore. For instance, multiplexing ability can be doubled (e.g., expanded by a factor of 2) for a color channel and use of a first fluorophore that is photobleaching resistant when irradiated using the color channel, and a second fluorophore that is photobleachable when irradiated using the color channel. Additional examples are provided below.

In variations, the dye(s)/fluorophore(s) can transition between states based upon application of a stimulus or stimuli, where the stimuli can involve one or more of: a stimulus involving irradiation, a stimulus involving a change in pH, a stimulus involving a change in temperature, a stimulus involving a change in pressure, a stimulus involving a change in electric field, a stimulus involving a change in magnetic field, or another suitable stimulus. Transition states of the dye(s)/fluorophore(s) can be binary (e.g., a first state and a second state) in response to an applied stimulus. Alternatively, a fluorophore can undergo transitions between a set of states (e.g., to different degrees), depending upon a method of application of the applied stimulus or stimuli, and/or number of same stimulus-response fluorophores attached to a target. For irradiation-responsive materials, stimulus application parameters can include intensity, wavelength, exposure duration, and other factors, and the amount of exposure to the stimulus can achieve different levels of photobleaching (which can have a more differentiable effect when multiple fluorophores are used to tag the same target). For pH-responsive materials, stimulus application parameters can include pH value, temperature, duration of exposure, and other factors and the amount of exposure to the stimulus can achieve different levels of photobleaching (which can have a more differentiable effect when multiple fluorophores are used to tag the same target). For temperature-responsive materials, stimulus application parameters can include temperature, duration of exposure, and other factors and the amount of exposure to the stimulus can achieve different levels of photobleaching (which can have a more differentiable effect when multiple fluorophores are used to tag the same target).

For multiplexing, the set of processing materials can include materials for tagging groups of dyes/fluorophores including one or more dyes/fluorophores that are resistant to the stimulus (or are not responsive to application of the stimuli) for a respective color channel, and one or more dyes/fluorophores that are sensitive to the stimulus.

Examples of photostimulus-responsive dyes/fluorophores include: Atto 495 (Blue color channel), FAM (Blue color channel), Bodipy-TMR (Green color channel), ROX (Yellow color channel), Cyanine 5 (Red color channel), Dy636 (Red color channel), Atto680 (Crimson color channel), and Cyanine 5.5 (Crimson color channel). Examples of photostimulus-resistant dyes/fluorophores include: Dy490 (Blue color channel), Atto488 (Blue color channel), Alexa488 (Blue color channel), Cyanine 3 (Green color channel), AttoRho 6G (Green color channel), HEX (Green color channel), VIC (Green color channel), SUN (Green color channel), Rhodamin 6G (Green color channel), Atto532 (Green color channel), Cyanin 3.5 (Yellow color channel), TEX615 (Orange color channel), Texas Red (Orange color channel), CAL Fluor 610 (Orange color channel), Bodipy-TR-X (Orange color channel), Atto590 (Orange color channel), Atto647N (Red color channel), and Dy682 (Crimson color channel).

Examples of pH sensitive fluorophores include pHrodo™ Green AM, pHrodo™ Red AM, fluorescein, LysoSensor Yellow, LysoSensor Blue, LysoSensor Green, Oregon Green 514, Oregon Green 488, Dichlorofluorescein derivatives, ACMA, HPTS, FAM, pHluorin, and pHluorin2.

Examples of temperature sensitive fluorophores include rhodamine B, Rhodamine 6G, Rhodamine C, Benzothiadiazoles, aza-BODIPY, phthalocyanines, perylene bisimide, and others.

Fluorophores or other colorimetric indicators can be differentially-responsive to the stimuli discussed, such that an applied stimulus produces differential responses in the fluorophores/colorimetric indicators. Alternatively, fluorophores or other colorimetric indicators can be equally-responsive or near-equally-responsive to an applied stimulus.

As such, implementation of the methods described can involve exposing tagged target analytes with stimulus-responsive tagging components, which can be differentially detectable before and/or after application of a stimulus, thereby increasing the level of plexy achievable with a limited number of color channels.

Figure 3K:
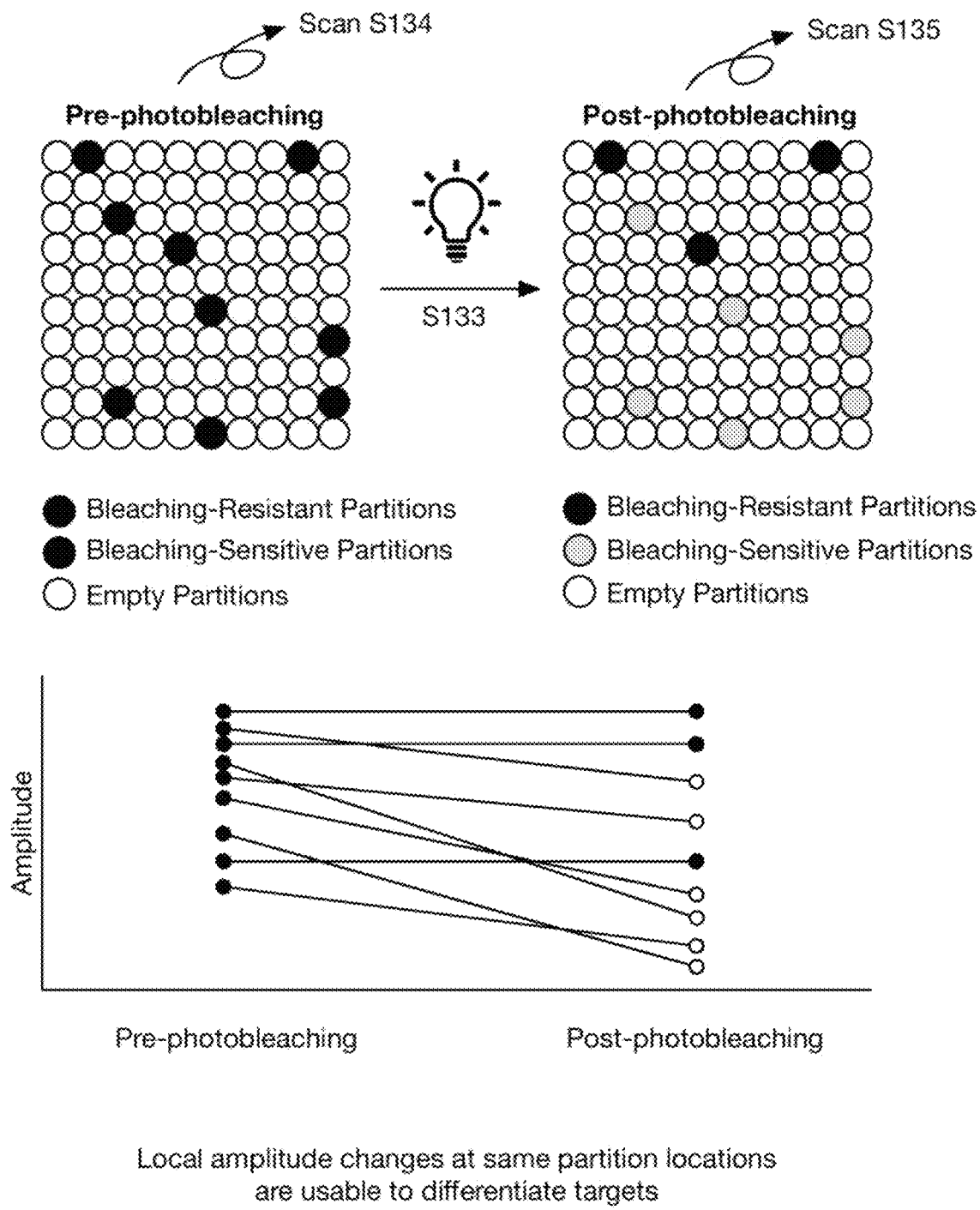
FIG. 3K depicts a schematic of an example of stimulus-responsive probes used for tagging and detection of different targets.

In relation to Step S130, the method 100 can additionally or alternatively include (for one or more color channels of a set of color channels involved in detection, and for a first fluorophore of the set of processing materials) use of a first fluorophore for achieving higher degrees of multiplexing, wherein the first fluorophore is a stimulus-responsive (e.g., photo-bleachable, photo-responsive, pH responsive, temperature-sensitive, etc.) fluorophore, and wherein detecting signals from the set of partitions comprises scanning the set of partitions prior to and post applying a stimulus to the first fluorophore, thereby transitioning the first fluorophore between a first state and a second state S133 (an example of which is shown in FIG. 3K). In a specific example, the applied stimulus is a light stimulus, and scanning can be performed with a first wavelength range of light to detect signals from the set of partitions prior to photobleaching, and after a second wavelength range of light configured to bleach the first fluorophore is applied. As such, the method 100 can include detecting signals from the set of partitions in a first phase of analysis upon scanning the set of partitions with the first wavelength range of light S134, and detecting signals from the set of partitions in a second phase of analysis upon scanning the set of partitions and bleaching the first fluorophore with the second wavelength range of light S135, as shown in FIG. 3K. As such, the set of processing materials described can include at least one primer structured to tag a first target with a first probe having a first fluorophore and a second target with a second probe having a second fluorophore, wherein the first fluorophore is a photo-bleachable fluorophore, thereby enabling differential detection of the first target and the second target. Alternatively, for Taqman™ chemistry, the set of processing materials can include, for a first target and a second target of the set of targets: a primer set comprising: a first primer structured to tag the first target with a first probe having a first fluorophore and a second primer structured to tag the second target with a second probe having a second fluorophore, wherein the first fluorophore is a photo-bleachable fluorophore, and wherein detecting signals from the set of partitions includes scanning the set of partitions with a first wavelength range of light and a second wavelength range of light configured to bleach the first fluorophore, thereby enabling differential detection of the first target and the second target.

Wavelengths of light used for scanning can be in the visible or non-visible spectrum. Light sources implemented can include laser light, light emitting diodes (LEDs), and/or other light sources. Laser powers implemented can include laser powers of 10 mW through 80 mW (or alternatively less than 10 mW or greater than 80 mW laser powers). However, other low power lasers can be implemented.

In a specific example, where the first fluorophore is FAM, scanning the set of partitions can include: scanning a set of planes of partitions within a collecting container, with a laser having a power of 50 mW and focused with optics to a 20 micron-thick light sheet (where other thicknesses less than 20 microns or greater than 20 microns can be implemented), where the duration of scanning for the set of planes (e.g., 500 planes) is at most 3 minutes, and wherein scanning bleaches the first fluorophore. Bleaching can be performed across a single scan of the set of planes, or across multiple scans of the set of planes. However, variations of the specific example can use other light sources (e.g., LEDs) that are lower power, with longer exposure times to achieve bleaching or other states of signal emission characteristics. Detecting signals from the set of partitions can be performed prior to bleaching in a first characterization of the set of partitions, and post bleaching the first fluorophore for a second characterization of the set of partitions, in order to achieve higher degrees of multiplexing for differential detection of targets based upon the first characterization and the second characterization. Given that the locations of the partitions do not change (e.g., are fixed in position within a stable emulsion), the first characterization can describe a first local signal amplitude for each droplet, and the second characterization can describe a second local signal amplitude for each droplet after the light stimulus is applied, where local amplitude characterizations can be achieved for partitions arranged in bulk with embodiments, variations, and examples of the platforms described.

Furthermore, scanning can be performed using different light wavelengths, powers, exposure times, and other parameters, for other transitionable fluorophores implemented in addition to the first fluorophore.

An example of signal discrimination pre and post photobleaching is shown in FIG. 3K.

Alternatively, for primarily non-photo responsive fluorophores, scanning the set of partitions can include: scanning a set of planes of partitions within a collecting container prior to application of a stimulus (e.g., temperature change, electric field, pH shift, mechanical stimulus, etc.); detecting signals from the set of planes of partitions for a first characterization of the set of partitions; scanning the set of planes of partitions within the collecting container post application of the stimulus (e.g., temperature change, electric field, pH shift, mechanical stimulus, etc.); detecting signals from the set of planes of partitions for a second characterization of the set of partitions; and characterizing targets of the sample in a multiplexed manner based upon the first characterization and the second characterization.

As such, in relation to other stimuli, the method 100 can include scanning the set of partitions with other wavelength(s) of light prior to and/or post-application of a stimulus (e.g., temperature change, electric field, pH shift, mechanical stimulus, etc.), where the stimulus causes changes in signal emission from the set of partitions appropriate to the wavelength(s) of light used for scanning.

2.1.5 Multiplexing with Different Levels of Plexy at Different Regions of a Density Gradient In variations where the set of partitions comprise droplets of an emulsion, the emulsion can include subregions at different depths within the collecting container (e.g., vertical depths, radial depths, etc.), each subregion associated with a different level of plexy. For instance, a first subregion of the emulsion can include a first sample being assessed for targets of a first panel, and a second subregion of the emulsion can include a second sample being assessed for targets of a second panel, where the degree of multiplexing required to characterize the first panel of targets of the first sample is different from the degree of multiplexing required to characterized the second panel of targets of the second sample.

In variations where the emulsion is generated upon applying a force (e.g., centrifugal force, pressure, etc.) to the sample(s) through a porous membrane or plate with openings, the first sample can have a first density and the second sample can have a second density, such that the first sample and the second sample self-arrange at different depths of the collecting container and have processing materials for different levels of plexy, at each depth of the collecting container. However, a gradient of regions can be formed in another suitable manner, in order to have different levels of assay plexy at different subregions of the collecting container, for different sets of targets of different samples.

2.1.6 Combined Multiplexing Options to Further Expand Levels of Plexy

In relation to the variations of multiplexing described (e.g., with color combinatorics, with stimulus-responsive materials, with density gradients involving layers of a container each having different degrees of plexy, etc.), multiplexing can be performed in a combinatorial manner, by implementing a number of different strategies, including color combinatorics, signal amplitude-based multiplexing (e.g., where discrimination of various targets is based upon signal amplitude with varied concentrations of primers, and when levels of background noise allow for accurate characterizations of signal amplitude corresponding to each target), stimulus-responsive fluorophores/dyes, different amplification and tagging chemistries (e.g., TaqMan-based chemistries described in more detail below, KASP-based chemistries, etc.) where a first level of plexy can be achieved with a first chemistry/assay design and a second level of plexy can be achieved with a second chemistry/assay design, chemistries involving Foerster resonance energy transfer (FRET) to produce a cascade of emission for different partitions, chemistries of the set of processing materials with non-hydrolysis probes, and other multiplexing technologies. For instance, chemistries with non-hydrolysis probes that are capable of FRET behavior can be used to tag the set of targets with a set of permutations of the set of non-hydrolysis probes, where detecting signals from the set of partitions comprises detecting signals (e.g., based upon FRET from a first fluorophore of a first non-hydrolysis probe to a second fluorophore of a second non-hydrolysis probe) corresponding to the set of permutations, for differential detection of the set of targets. Additionally or alternatively, the set of processing materials can include a set of hydrolysis probes, such that the method includes tagging the set of targets with a set of combinations of the set of hydrolysis probes, and wherein detecting signals from the set of partitions includes detecting signals corresponding to the set of combinations for differential detection of the set of targets.

Figure 4A:
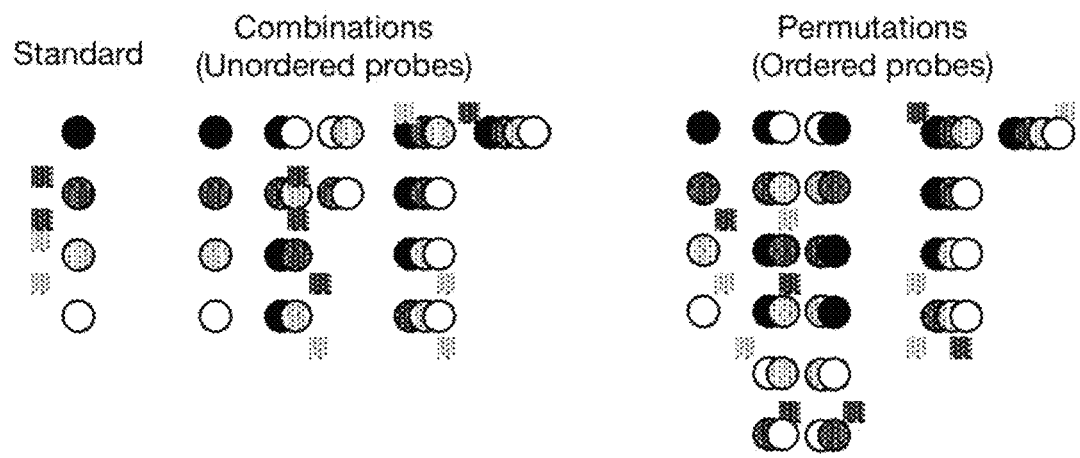
FIG. 4A depicts a schematic of achievable levels of multiplexing, with combinations and permutations of probes and detected colors.

FIG. 4A shows the number of different targets that can be differentially tagged with four colors, without combinations or permutations of colors, with combinations of colors, and with permutations of colors. Without combinations or permutations of colors, four different targets can be differentially tagged and detected using four colors. With combinations four colors (with position-agnostic arrangements/orders of the colors used to tag the respective targets), 15 different targets can be differentially tagged and detected using four colors, and 10 different targets can be differentially tagged and detected using four colors if only up to two colors are selected from the set of four colors. With permutations of four colors (with position-sensitive arrangements/orders of the colors used to tag the respective targets), 21 different targets can be differentially tagged and detected using four colors (with two colors of tandem probes), and 16 different targets can be differentially tagged and detected using four colors if only up to two colors are selected from the set of four colors.

Figure 4B:
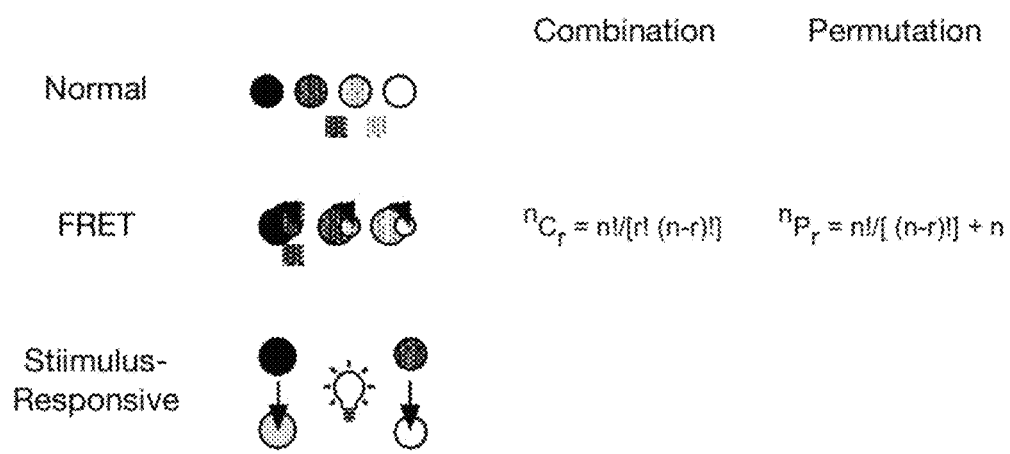
FIG. 4B depicts a schematic demonstrating expansion of multiplexing ability for an assay, with combinations of multiplexing strategies.

As described above, the levels of multiplexing achieved can be enhanced (e.g., in an additive manner) with co-implementation of multiple multiplexing strategies and mechanisms. As shown in FIG. 4B, when combinations of colors are used, the number of targets that can be differentially tagged can be represented by expression [1] below, where n represents the number of available colors, and r represents the number of selected colors from the number of available colors. When permutations of colors are used, the number of targets that can be differentially tagged can be represented by expression [2], where n represents the number of available colors, and r represents the number of selected colors from the number of available colors.

$$nCr = n!/[r!(n-r)!] \quad [1]$$

$$nPr = n!/[(n-r)!] + n \quad [2]$$

Thus, with four available colors and up to three colors used in combination to tag targets, the number of targets that can be differentially tagged is 14. With four available colors and only 2 colors used in permutation to tag targets, the number of targets that can be differentially tagged is 12.

When involving probes capable of FRET behavior, with four available base colors and 3 additional FRET-discriminable colors for a total of 7 signal types used in combination to tag targets, the number of targets that can be differentially tagged is 63 if up to 3 signal types are selected and 28 if up to two signal types are selected.

When additionally involving photobleachable probes, with four available base colors, 3 additional FRET-discriminable colors, and 2 photobleachable probes for a total of 9 signal types used in combination to tag targets, the number of targets that can be differentially tagged is 127 if up to 3 signal types are selected and 45 if up to two signal types are selected.

As such, the methods, systems, and compositions described can achieve extremely high levels of multiplexing even when a 3D imaging technique (e.g., light sheet imaging, 3D confocal microscopy, etc.) is involved for target detection, where background noise is much higher than for systems (e.g., microwell systems, etc.) where 1D and 2D imaging techniques are sufficient for target detection.

2.1.7 Method—Assay Materials and Compositions Involving Allele-Targeting Probes

In alternative variations, the set of processing materials can utilize, for each target, a set of fluorophore-conjugated versions of the same probe sequence, where the set of fluorophore-conjugated versions produce a detectable combination of signals (e.g., color signals) that enable positive identification of the respective target. As such, the set of fluorophore-conjugated versions for each respective probe sequences can enable multiplexing based on color combinatorics to provide a high degree of multiplexing. In more detail, the set of processing materials can include: a) for a respective target region of the set of targets, a forward primer, a reverse primer, and a set of fluorophore-conjugated probes, each of the set of fluorophore-conjugated probes targeting an allele of the respective target region and b) a master mixture including amplification reagents. The set of processing materials can additionally or alternatively include a probe additive for each of the set of fluorophore-conjugated probes, where the probe additive functions to quench background fluorescence resulting from the probes (i.e., is structured to reduce background noise), thereby improving signal-to-noise ratio (SNR). The set of fluorophore-conjugated probes can thus be configured to tag different alleles within a partition with different combinations of colors (corresponding to different fluorophores used), in order to provide discrimination of partition contents upon detection of signals from contents of each partition. A probe additive reagent can further include one or more quenches structured to interact with at least one of the 3' region and the 5' region of a fluorophore-labeled oligonucleotide.

Figure 5A:
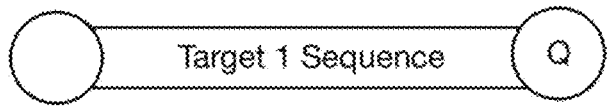
FIG. 5A depicts alternative assay chemistry for performing differential detection and quantitation of targets in a multiplexed manner.
Figure 5A:
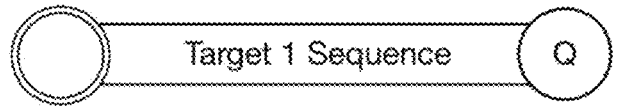
Figure 5A:
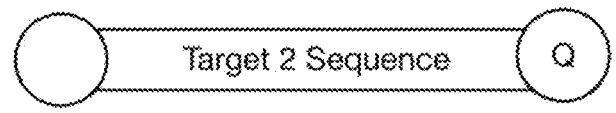
Figure 5A:
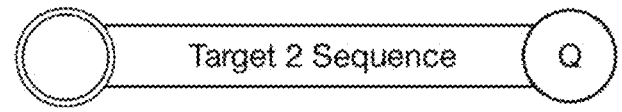
Figure 5A:
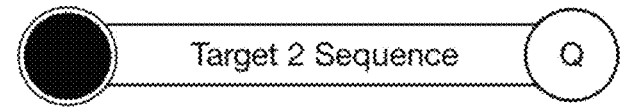
Figure 5A:

FIG. 5A depicts an example of fluorophore-conjugated probes that provide target detection and digital quantitation of different targets based on color combinatorics.

The probe additive can have a melting temperature (Tm) of 40-48° C. to be non-reacting during thermocycling (above 55° C. in general). However, in variations, the Tm of the probe additive can be greater than 48° C. or greater than 55° C. In examples the Tm of the probe additive can be from 47-79° C., greater than or equal to 79° C., or an intermediate value. In particular, with implementation of multiple and different probe additives, as primer diversity increases, primers can effectively compete with the probe additives to bind to respective probes, and some of the undesired primer-probe interactions cannot be eliminated via in silico design alone.

The set of probes can include Taqma™ probes and/or other dual-labeled probes to differentiate alleles of a target region. Probes can include dyes/fluorophores associated with chemical families including: acridine derivatives, arylmethine derivatives, anthracene derivatives, tetrapyrrole derivatives, xanthene derivatives, oxazine derivatives, dipyrromethene derivatives, cyanine derivatives, squaraine derivates, squaraine rotaxane derivatives, naphthalene derivatives, coumarin derivatives, oxadiazole derivatives, pyrene derivatives, and/or other chemicals. Such fluorophores can further be attached to other functional groups as needed for tagging of targets in a detectable manner. Dyes/fluorophores can additionally or alternatively include compositions described in Section 2.1.1 above.

Primer concentration (e.g., forward primer concentration), probe concentration, and probe additive concentrations can be configured to improve detection performance (e.g., in relation to number of positive counts corresponding to positive targets, in relation to SNR values, etc.). In variations, the primer concentration (e.g., forward primer concentration):probe concentration:probe additive concentration can have a ratio of: 10:10:30; 10:20:60; 10:40:120; 10:80:240; 20:10:30; 20:20:30; 20:20:60; 20:40:120; 20:80:240; 40:10:30; 40:20:60; 40:40:120; 40:80:240; 80:10:30; 80:20:60; 80:40:120; 80:80:240; ratio values intermediate to those described; or other ratio values. Concentrations can be provided in terms of molarity or another suitable unit.

The example of targets (e.g., SNPs) and corresponding tagged-color combinations for detection and differentiation shown in FIGS. 3A and 3B can be similarly detected using the set of processing materials described here in Section 2.1.2. Similarly, the example shown in FIGS. 3C and 3D can be adapted for systems greater than 5 colors or less than 4 colors.

Quenchers of Taqman™ and/or other dual-label probes can be configured to quench signal of the fluorophore if the quencher is in proximity to the fluorophore below a threshold distance). Additionally or alternatively, quenchers can include one or more of: black hole quenchers, static quenchers, self-quenchers (e.g., fluorophores that self-quench under certain conditions by producing secondary structures or other structures), and/or other suitable quenchers. Quenchers can be used to suppress background signals (e.g., for 3D imaging applications, for other detection applications).

However, the set of processing materials can additionally or alternatively include other suitable components and/or be configured in another suitable manner.

2.2 Method—Partitioning of Sample with Processing Materials

Distributing the sample combined with the set of processing materials, across a set of partitions in step S140 can include receiving a sample (variations and examples of which are described above) at a vessel passively or actively (e.g., with applied force, such as with gravitational force, with centrifugal force, with pressurization, etc.). The sample and processing materials can be delivered manually (e.g., with a fluid aspiration and delivery device, such as a pipettor). The sample and processing materials can additionally or alternatively be delivered with automation (e.g., using liquid handling apparatus or other sample handling apparatus).

In variations, vessel formats can include: tubes (e.g., PCR tubes) containing partitions of the sample (e.g., in droplet format, in emulsion format, in another format), wells (e.g., microwells, nanowells, etc.), channels, chambers, and/or other suitable containers. Additionally or alternatively, alternative variations of step S130 can include receiving the sample at other suitable substrates (e.g., slides, plates, etc.) functionalized with material components structured to interact with target material of the sample. For instance, sample material can be spotted onto substrates with material components structured to interact with target material of the sample and in a detectable manner.

Figure 6:
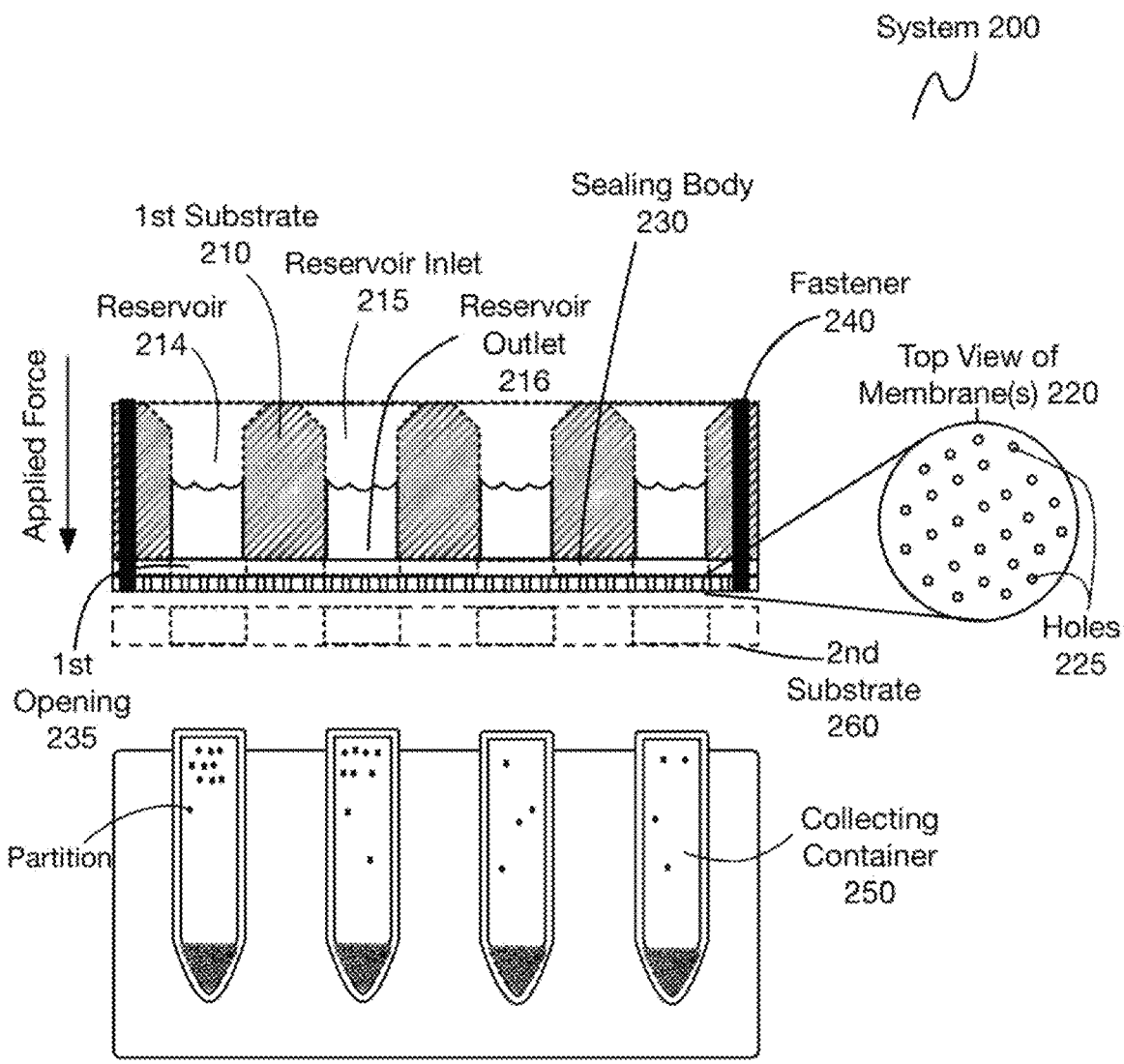
FIG. 6 depicts a schematic of an embodiment of a system for partitioning samples.

Embodiments, variations, and examples of the methods described can be implemented by or by way of embodiments, variations, and examples of components of system 200 shown in FIG. 6, with a first substrate 210 defining a set of reservoirs 214 (for carrying sample/mixtures for droplet generation), each having a reservoir inlet 215 and a reservoir outlet 216; one or more membranes (or alternatively, droplet-generating substrates) 220 positioned adjacent to reservoir outlets of the set of reservoirs 214, each of the one or more membranes 220 including a distribution of holes 225; and optionally, a sealing body 230 positioned adjacent to the one or more membranes 120 and including a set of openings 235 aligned with the set of reservoirs 214; and optionally, one or more fasteners (including fastener 240) configured to retain the first substrate 210, the one or more membranes 220, and optional sealing body 230 in position relative to a set of collecting containers 250. In variations, the system 200 can additionally include a second substrate 260, wherein the one or more membranes 220 and optionally, the sealing body 230, are retained in position between the first substrate 210 and the second substrate 260 by the one or more fasteners. In using embodiments, variations, and examples of the system 200, material derived from each sample is retained in its own tube and does not require batching and pooling, allowing for scalable batch size.

In variations, the distribution of holes 225 can be generated in bulk material with specified hole diameter(s), hole depth(s) (e.g., in relation to membrane thickness), aspect ratio(s), hole density, and hole orientation, where, in combination with fluid parameters, the structure of the membrane can achieve desired flow rate characteristics, with reduced or eliminated polydispersity and merging, suitable stresses (e.g., shear stresses) that do not compromise the single cells but allow for partitioning of the single cells, and steady formation of droplets (e.g., without jetting of fluid from holes of the membrane).

In variations, the hole diameter can range from 0.02 micrometers to 30 micrometers, and in examples, the holes can have an average hole diameter of 0.02 micrometers, 0.04 micrometers, 0.06 micrometers, 0.08 micrometers, 0.1 micrometers, 0.5 micrometers, 1 micrometers, 2 micrometers, 3 micrometers, 4 micrometers, 5 micrometers, 6 micrometers, 7 micrometers, 8 micrometers, 9 micrometers, 10 micrometers, 20 micrometers, 30 micrometers, any intermediate value, or greater than 30 micrometers (e.g., with use of membrane having a thickness greater than or otherwise contributing to a hole depth greater than 100 micrometers).

In variations, the hole depth can range from 1 micrometer to 200 micrometers (e.g., in relation to thickness of the membrane layer) or greater, and in examples the hole depth (e.g., as governed by membrane thickness) can be 1 micrometers, 5 micrometers, 10 micrometers, 20 micrometers, 30 micrometers, 40 micrometers, 50 micrometers, 60 micrometers, 70 micrometers, 80 micrometers, 90 micrometers, 100 micrometers, 125 micrometers, 150 micrometers, 175 micrometers, 200 micrometers, or any intermediate value.

In variations, the hole aspect ratio can range from 5:1 to 200:1, and in examples, the hole aspect ratio can be 5:1, 10:1, 20:1, 30:1, 40:1, 50:1, 60:1, 70:1, 80:1, 90:1, 100:1, 125:1, 150:1, 175:1, 200:1, or any intermediate value.

In variations, the hole-to-hole spacing can range from 5 micrometers to 200 micrometers or greater, and in examples, the hole-to-hole spacing is 5 micrometers, 10 micrometers, 20 micrometers, 30 micrometers, 40 micrometers, 50 micrometers, 60 micrometers, 70 micrometers, 80 micrometers, 90 micrometers, 100 micrometers, 125 micrometers, 150 micrometers, 175 micrometers, 200 micrometers, or greater. In a specific example, the hole-to-hole spacing is greater than 10 micrometers.

In examples, the hole orientation can be substantially vertical (e.g., during use in relation to a predominant gravitational force), otherwise aligned with a direction of applied force through the distribution of holes, or at another suitable angle relative to a reference plane of the membrane or other droplet generating substrate 120.

Additionally or alternatively, embodiments, variations, and examples of the methods described can be implemented by or by way of embodiments, variations, and examples of components described in U.S. application Ser. No. 17/687,080 filed 4 Mar. 2022, U.S. Pat. No. 11,242,558 granted 8 Feb. 2022, U.S. application Ser. No. 16/309,093 filed 25 May 2017, and PCT Application PCT/CN2019/093241 filed 27 Jun. 2019, each of which is herein incorporated in its entirety by this reference. However, methods described can additionally or alternatively implement other system elements for sample reception and processing.

2.3 Method—Target-Specific Tagging and Amplification

Step S150 recites: performing target-specific (e.g., allele-specific) tagging and amplification (and/or providing suitable environments for supporting such operations), with the set of processing materials, for target regions associated with the set of targets across a set of stages. Step S150 and associated Steps S151, S152, and S153 (described in more detail below and in shown in the schematic of FIG. 7 and FIG. 8) preferably occur within partitions generated from the sample.

In one embodiment, the sample can be combined with an embodiment, variation, or example of the set of processing materials described above, and then partitioned such that template molecules of the sample occupy individual partitions with minimal overlap between different template molecules. Partitioning can be performed by passing the sample combined with the set of processing materials through a partitioning device (e.g., to generate droplets, to generate an emulsion with droplets provided in a continuous phase, etc.). Partitioning can alternatively be performed by distribution of the sample combined with the set of processing materials across a set of containers (e.g., microwells, nanowells, etc.). Partitioning can still alternatively be performed by distributing the sample combined with the set of processing materials across a substrate (e.g., as spots) and/or in another suitable manner.

Figure 7:
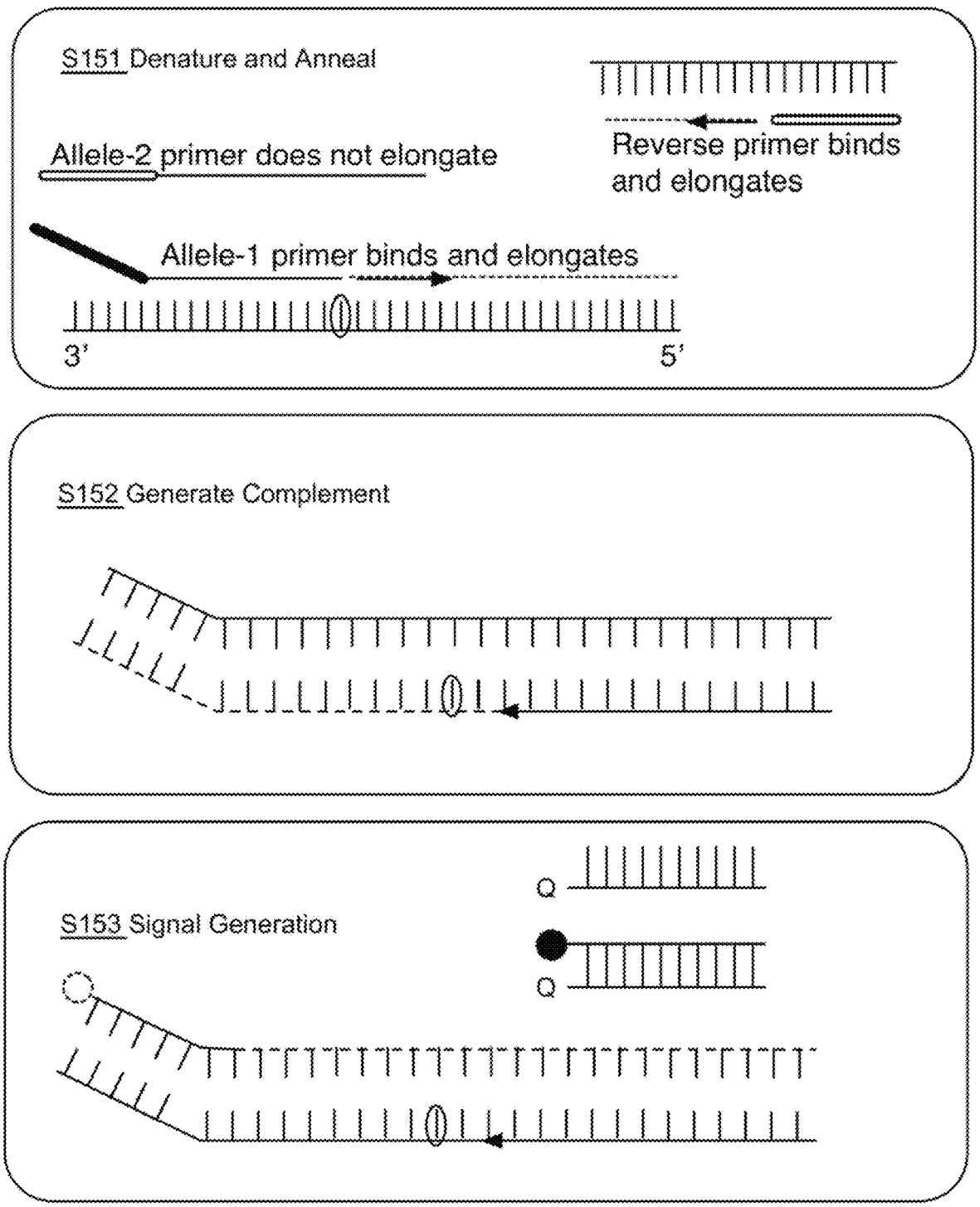
FIG. 7 depicts schematics of portions of an embodiment of a method for detection of one of the targets in a multiplex panel.
Figure 8:
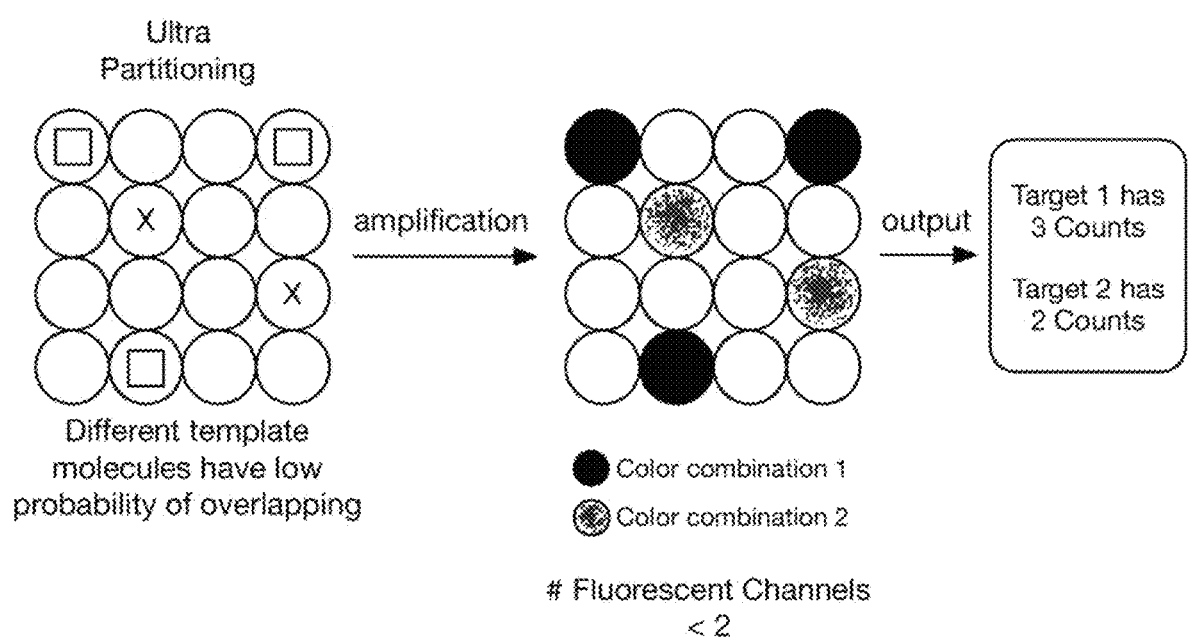
FIG. 8 depicts a schematic related to digital quantitation of targets (e.g., where the number of targets is greater than the number of fluorescent channels).

As shown in FIG. 7, Step S150 functions to denature the template material (e.g., DNA template) of the sample, anneal components to the target region(s) being evaluated, and amplify the target region(s) in a first stage, with generation of complements of allele-specific tail sequences in a second stage. Then, in subsequent stages of amplification, amounts of allele-specific tagged sequences increase in a manner that can be detected (e.g., through an optical-based detection method).

As shown in FIG. 7, the first stage of sample processing S151 can include denaturing of sample material (e.g., sample DNA) and processing the denatured sample material with primers (i.e., allele-specific forward primers grouped with corresponding reverse primers for each target). In the first stage, one of the allele-specific forward primers of the set of sample processing materials matches the target (e.g., target SNP) and, with the common reverse primer, amplifies the target region. As such, targets (e.g., target SNPs) present in the sample are amplified upon interacting with respective allele-specific forward primers.

As shown in FIG. 7, the second stage of sample processing S152 can include generation of allele-specific sequences (e.g., tail sequences), where the common reverse primer binds to, elongates, and produces a complementary copy of a labeled tail sequence corresponding to the target allele.

As shown in FIG. 7, the third stage of sample processing S153 and subsequent stages can include one or more rounds of amplification/PCR to produce a detectable signal, whereby levels of tagged allele-specific sequences increase until a detection threshold is reached and/or surpassed. In the third stage S153 and subsequent stages of sample processing, labeled oligonucleotides bind to new complementary sequences (e.g., tail sequences), releasing fluorophores from corresponding quenchers to produce detectable signals for each target (e.g., target SNP, other target) present in the sample. However, fluorophores corresponding to targets that are not present are not released and thus continue to be quenched during rounds of amplification. In particular, with regard to parameters associated with threshold cycles at which or beyond which amplified targets become detectable (e.g., Ct, Cp, Cq, etc.), step S153 can include detecting and/or returning results indicative of target presence prior to the end-point of the process and/or at the end-point of the process (e.g., as in end-point PCR). Additionally or alternatively, real-time measurement of signals can be performed contemporaneously with each cycle of amplification.

In relation to the one or more stages of sample processing, activation-associated steps can be performed at a temperature or temperature profile (e.g., 90° C., 92° C., 94° C., another suitable temperature), for a duration of time (e.g., 10 minutes, 12 minutes, 15 minutes, another suitable duration of time), and/or for a number of cycles (e.g., 1 cycle, 2 cycles, another suitable number of cycles). In relation to the one or more stages of sample processing, denaturation-associated steps can be performed at a temperature (e.g., 90° C., 92° C., 94° C., another suitable temperature) or temperature profile, for a duration of time (e.g., 10 seconds, 15 seconds, 20 seconds, 25 seconds, another suitable duration of time), and/or for a number of cycles (e.g., 1 cycle, 5 cycles, 10 cycles, 20 cycles, another suitable number of cycles). In relation to the one or more stages of sample processing, annealing/elongation-associated steps can be performed at a temperature or temperature profile (e.g., 52-70° C. with a ramp down rate, another suitable temperature profile), for a duration of time (e.g., 20 seconds, 30 seconds, 60 seconds, 90 seconds, another suitable duration of time), and/or for a number of cycles (e.g., 1 cycle, 5 cycles, 10 cycles, 20 cycles, 25 cycles, 30 cycles, another suitable number of cycles).

In a specific example, activation-associated steps in a first stage of sample processing can be performed at a temperature of 94° C., for 15 minutes, with 1 cycle. In the specific example, denaturation-associated steps in a second stage of processing can be performed at 94° C. for 20 seconds, with annealing/elongation performed from 61-55° C. (with a drop of 0.6° C./cycle), for 60 seconds and for 10 cycles. In the specific example, denaturation-associated steps in a third stage of processing can be performed at 94° C. for 20 seconds, with annealing/elongation performed at 55° C. for 60 seconds and for 26 cycles. Additional denaturation-associated steps can be performed at 94° C. for 20 seconds, with annealing/elongation performed at 57° C. for a suitable number of cycles (e.g., 3 cycles).

In another specific example, activation-associated steps in a first stage of sample processing can be performed at a temperature of 94° C., for 15 minutes, with 1 cycle. In the specific example, denaturation-associated steps in a second stage of processing can be performed at 94° C. for 20 seconds, with annealing/elongation performed from 65-57° C. (with a drop of 0.8° C./cycle), for 60 seconds and for 10 cycles. In the specific example, denaturation-associated steps in a third stage of processing can be performed at 94° C. for 20 seconds, with annealing/elongation performed at 57° C. for 60 seconds and for 30 cycles. Additional denaturation-associated steps can be performed at 94° C. for 20 seconds, with annealing/elongation performed at 57° C. for a suitable number of cycles (e.g., 3 cycles).

Stages of sample processing in Block S150 can further include implementation of additives (described in Section 2 above) to improve signal-to-noise ratio (SNR) characteristics in the context of multiplexed detection, by increasing signal characteristics and/or reducing background (e.g., noise other artifacts). Additionally or alternatively, stages of sample processing in Step S150 can implement other components (e.g., density gradient mediums) to improve SNR.

In particular, in the context of emulsion digital PCR with the numbers of partitions described, such multiplexed assay design aspects described can produce significantly improved signal-to-noise (SNR) values with reduced background, in relation to detection techniques described below (e.g., based on lightsheet imaging, etc.). In examples, target signals can be at least $10^2$ greater than background noise signals, $10^3$ greater than background noise signals, $10^4$ greater than background noise signals, $10^5$ greater than background noise signals, $10^6$ greater than background noise signals, $10^7$ greater than background noise signals, or better. Background noise can be attributed to fluorescence from adjacent partitions and adjacent planes of the set of planes of partitions in the context of emulsion digital PCR, or attributed to other sources with closely-positioned partitions. Determining the SNR can include scanning a set of planes of the set of partitions, determining a target signal value and a noise signal value for the set of planes, and determining the SNR from the target signal value and the noise signal value S180, where a variation of determining the target signal value and the noise signal value is described below.

Figure 5B:
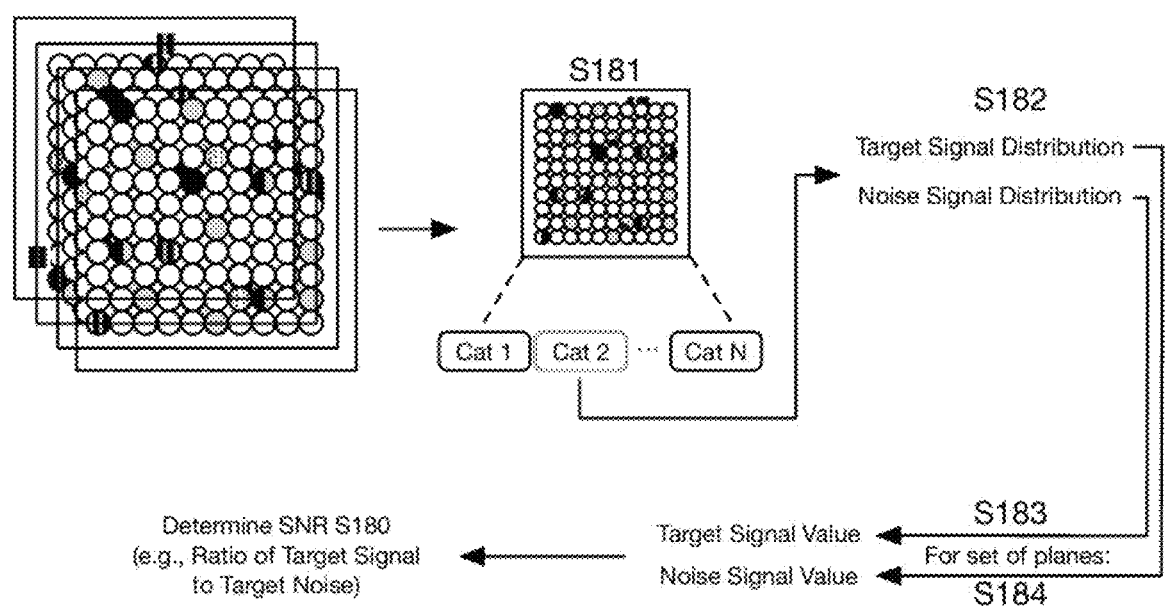
FIG. 5B depicts an embodiment of a process for determining a signal to noise ratio (SNR) for an embodiment of a digital multiplexed analysis.

In examples associated with reaction materials described and used for droplet digital PCR, determining the target signal value and a noise signal value can include: for each plane of a set of planes of partitions under interrogation (e.g., by lightsheet detection, fluorescent microscopy, confocal microscopy, detection by photodiodes, by another method of detection, etc.): determining a categorization (of a set of categorizations for the respective plane) based upon a profile of signal-positive partitions represented in a respective plane S181, determining a target signal distribution and a noise signal distribution specific to the profile S182. Here, a target signal value can be determined from the target signal distribution S183, and can be an average value (or other representative value) of the target signal intensities determined from the set of planes. Similarly, a noise signal value can be determined from the noise signal distribution S184, and the background noise signal value can be an average value (or other representative value) of the noise signal intensities determined from the set of planes. A schematic is shown in FIG. 5B.

However, materials used for the amplification and/or detection reactions can be otherwise configured to improve SNR.

2.4 Method—Signal Detection and Returned Outputs

As shown in FIG. 1A, the method 100 can include Step S110, which recites detecting signals indicative of a profile of a set of targets, from a processed sample (e.g., within a single vessel, within a set of vessels) Silo. Step S110 functions to enable detection of signals from dyes/fluorophores that are released upon processing the sample with the set of processing materials, thereby providing indications of presence of targets (e.g., SNP targets, other targets) within the sample. In particular, with regard to parameters associated with threshold cycles at which or beyond which amplified targets become detectable (e.g., Ct, Cp, Cq, etc.), step S110 can include detecting and/or returning results indicative of target presence prior to the end-point of the process and/or at the end-point of the process (e.g., as in end-point PCR). Additionally or alternatively, real-time measurement of signals can be perform contemporaneously with each cycle of amplification.

Processed sample material can include samples processed according to methods described above, with respect to multiplexed tagging of alleles of targets of interest.

In variations, detection of signals can include irradiating processed sample material with suitable excitation wavelengths of light, and/or receiving emitted wavelengths of light corresponding to released dyes/fluorophores. As such detection of signals can be implemented by an optical signal detection subsystem (e.g., imaging subsystem), including embodiments, variations, and examples of systems described above. In particular, detection subsystems can be structured for detection of signals from partitions (e.g., by light sheet imaging, by fluorescence microscopy, by confocal microscopy, by another suitable optical detection subsystem, etc.) using combinations of filters and/or color channels, where signals from individual partitions are detected in a high-partition number but low-occupancy regime. As such, detection can be performed for partitions arranged in 3D (e.g., as in droplets of an emulsion within a container), in 2D (e.g., for a monolayer or bi-layer of partitions at a substrate), and/or in another suitable format.

In variations, the sample can be processed with the set of processing materials in coordination with distribution of the sample across a set of partitions, where the set of partitions can include droplets (e.g., droplets of an emulsion, droplets provided in a sheathing fluid, gel droplets, other forms of droplets), microchambers, microwells, spotted samples on a substrate, and/or other partitions. As such, the partitions can be provided within one or more of: a container configured for centrifugation (e.g., a centrifuge tube, a microcentrifuge tube, etc.), a process container for PCR (e.g., a PCR tube), a strip tube, a plate having wells (e.g., a microtiter plate, a multi-well plate, a microwell plate, a nanowell plate, etc.), or another suitable collecting container. Additionally or alternatively, partitions can include regions of sample provided in another manner upon a substrate (e.g., spotted onto a substrate/slide).

With respect to sample processing using the set of processing materials, reactions within individual partitions can thus produce signals that are detected by systems that can detect signals from multiple partitions or all partitions simultaneously in a distinguishable manner (e.g., with a 3D scanning technique, as described above). Alternatively, reactions within individual partitions can produce signals that are detected by systems that can detect signals from individual partitions in a sequential manner.

Characterizing a set of targets of a sample (e.g., in relation to presence/absence, in relation to counts of targets), upon scanning the set of partitions, can include: generating a multivariable vector of emission values (e.g., emitted intensity values across the set of available color channels), for each detected emitted signal from a respective partition, paired with the excitation parameters used to excite the set of partitions (e.g., in the context of probes that exhibit FRET and/or probes that can be photobleached); performing a clustering operation with the multivariable vectors of emission values generated from the set of partitions; sorting partitions of the set of partitions into a set of categories corresponding to targets of the set of targets, based upon the clustering operation and a known set of probes used to tag the set of targets; and generating a count of each of the set of targets represented in the set of partitions, based upon said sorting. In variations, the clustering operation can include performance of a co-localization operation, whereby scanning deviations are corrected for in order to further delineate/provide stronger discrimination between different clusters of partitions. Additionally or alternatively, clustering algorithms can further include one or more of: principal component analysis (PCA), k-means clustering, t-stochastic neighbor embedding (t-SNE), UMAP clustering, and/or other algorithms. In variations, characterizing partitions can further include identifying partitions that are signal positive in more than one channel, in relation to color combinatorics described above.

Step S120 recites: returning a characterization of the processed sample based upon the profile. Step S120 functions to provide information pertaining to presence or absence of the set of targets associated with the sample being evaluated, and/or presence or absence of variants of the set of targets. The characterization can then be used to provide diagnostics and/or to support diagnostics of the organism(s) from which the processed sample was sourced, and/or to provide quality for conclusiveness of diagnostic results. Additionally or alternatively, the characterization can be used to guide provision of therapeutics (e.g., personalized therapeutics) corresponding to determined states of the organism(s) from which the processed sample was sourced, in order to improve or maintain health statuses of the organism(s).

In specific applications, the characterization can be used to inform diagnostics, provide other characterizations (e.g., of disease resistance, of disease predisposition, of genetic relationships, etc.) and/or guide generation of therapeutics associated with non-invasive prenatal testing (described above and in more detail below). More broadly, outputs of step S120 can be used to characterize (e.g., based on relative abundance measurements) self genetic material (e.g., genetic material of an organism) and non-self genetic material (e.g., genetic material not of the organism, genetic material of a different organism) from a sample.

Additionally or alternatively, in specific applications, the characterization can be used to inform characterizations of a subject from which the sample is sourced, in relation to one or more of: cancers, integumentary system conditions, skeletal system conditions, muscular system conditions, lymphatic system conditions, respiratory system conditions, digestive system conditions, nervous system conditions, endocrine system conditions, cardiovascular system conditions, urinary system conditions, reproductive system conditions, and/or other conditions.

Outputs can additionally or alternatively support at least one of: pathogen detection, non-invasive prenatal testing, organ transplantation analysis, forensics, and oncology, based upon the quantitative analysis.

In other specific applications, the characterization can be used to inform diagnostics, provide other characterizations (e.g., of disease resistance, of disease predisposition, of genetic relationships, etc.) and/or guide generation of therapeutics in the context of other multicellular organisms, plants, fungi, unicellular organisms, viruses, and/or other subjects.

2.5 Method—Signal Detection and Returned Outputs for Fetal Fraction and Non-Invasive Prenatal Testing Applications As shown in FIG. 1C, in a variation, a method 100b for determination of fetal fraction (FF) can include: Step S110c, which recites: detecting signals indicative of a profile of a set of single nucleotide polymorphisms from a sample. Step S110c functions to enable characterizations of presence or absence of alleles of a set of SNPs from a sample (e.g., a maternal sample, other sample), which can be used to determine FF and inform conclusiveness of results in NIPT applications. In particular, with regard to parameters associated with threshold cycles at which or beyond which amplified targets become detectable (e.g., Ct, Cp, Cq, etc.), step S110c can include detecting and/or returning results indicative of SNP allele presence prior to the end-point of the process and/or at the end-point of the process (e.g., as in end-point PCR).

Processed sample material can include samples processed according to methods described above, with respect to multiplexed tagging of alleles of SNPs of interest.

In variations, detection of signals can include irradiating processed sample material with suitable excitation wavelengths of light, and/or receiving emitted wavelengths of light corresponding to released dyes/fluorophores. As such detection of signals can be implemented by an optical signal detection subsystem (e.g., imaging subsystem), including embodiments, variations, and examples of systems described above. In particular, detection subsystems can be structured for detection of signals from partitions (e.g., by light sheet imaging, by another suitable optical detection subsystem, etc.) using combinations of filters and/or color channels, where signals from partitions are detected in a high-partition number but low-occupancy regime.

In variations, the sample can be processed with the set of processing materials in coordination with distribution of the sample across a set of partitions, where the set of partitions can include droplets (e.g., droplets of an emulsion, droplets provided in a sheathing fluid, gel droplets, other forms of droplets). Additionally or alternatively, the partitions can be provided within one or more of: a container configured for centrifugation (e.g., a centrifuge tube, a microcentrifuge tube, etc.), a process container for PCR (e.g., a PCR tube), a strip tube, a plate having wells (e.g., a microtiter plate, a multi-well plate, a microwell plate, a nanowell plate, etc.), or another suitable collecting container. Additionally or alternatively, partitions can include regions of sample provided in another manner upon a substrate (e.g., spotted onto a substrate/slide).

Step S120c recites: returning a characterization of relative abundance of alleles of each SNP in the set of SNPs to generate an estimate of fetal DNA fraction in the sample, which functions to enable determinations of conclusiveness of NIPT results.

In variations, SNP alleles processed and evaluated in a massively parallel manner to determine FF in step S120c can include SNPs associated with chromosomes 1, 13, 18, 21, X, and/or Y, at various loci (e.g., from 10 to 20,000 polymorphic loci); however, SNPs characterized to determine FF can additionally or alternatively be associated with other chromosomes and/or loci. SNPs evaluated can be biallelic or multiallelic, with more than two alleles per SNP. SNPs evaluated can further be characterized by a high minor allele fraction (MAF), with an MAF above a suitable threshold (e.g., MAF>0.2, MAF>0.3, MAF>0.4, etc.); however, SNPs evaluated can be characterized with other MAF values. SNPs evaluated can be for coding regions (e.g., synonymous, non-synonymous, missense, nonsense) and/or non-coding regions.

With respect to determination of FF in Step S120c, target panels undergoing evaluation can be designed such that FF associated with fetus of any gender can be determined, without requiring detection of chromosome Y markers. As such, for a male fetus, FF can be estimated by the amount of chromosome Y fragments present in the sample (e.g., maternal sample) relative to the amount of other non-sex chromosomes. For determination of FF for a female fetus, the set of SNPs evaluated are selected such that for each fetus-mother pair, there would be at least a few SNPs in the common SNP panel that are homozygous in mother and heterozygous in fetus. The count of the alternate allele from the fetus, when compared to the count of the homozygous allele (from mother, and also half from fetus), would yield FF for a female fetus (or non-male fetus, such as in intersex conditions).

In a specific application, the method can implement counting requirements per reference chromosome to provide indications of confidence in NIPT assay results with respect to threshold FF values. In a specific example, for a counting requirement of 400,000 counts per reference chromosome, the lowest FF (e.g., DNA FF) in which an aneuploidy assay would be confident in calling a true negative is ~4%; thus, the FF assay estimates <4% DNA FF, then the results from the aneuploidy assay would be inconclusive. However, if the FF assay estimates >4% DNA FF, then the results from the aneuploidy assay would be more conclusive with increasing FF.

However, in other specific examples, the counting requirement per reference chromosome can be set at another value (e.g., less than 400,000 counts, greater than 400,000 counts, etc.) in relation to other FF threshold values (e.g., 3%, 5%, 6%, other percentages, etc.).

Expansions of the methods can be applied to detection of sex aneuplodies (e.g., Klinefelter syndrome, Turner syndrome, etc.), trisomies (e.g., Downs syndrome, Edwards syndrome, Palau syndrome, etc.), and/or other genetic conditions.

2.6 Method—Signal Detection and Returned Outputs for Transplant Rejection Applications In another example, materials and methods described can be adapted for characterization and/or early detection of transplant rejection in a subject. Methods described here in Section 2.6 can be used to detect and digitally quantify donor-specific genetic material (e.g., dd-cfDNA, ds-DNA, GcfDNA) in a sample from a subject who has received a transplant, such that the sample potentially contains a quantifiable amount of self genetic material and donor genetic material. Furthermore, longitudinal characterization of the amount of donor genetic material in samples acquired from the subject at different time points can be used to assess onset of transplant rejection, where increases in donor genetic material over time can serve as a proxy for transplant rejection.

The biological rationale behind the utility of donor genetic material as a biomarker for transplant rejection is that the immune system of the subject receiving a transplant is activated upon recognition of the transplanted material (e.g., organ, cells, etc.) and produces antibodies in response. The antibodies attack the transplanted material, which leads to apoptosis or cell necrosis. The ruptured or dead cells then release their contents into the subject's blood plasma and thereafter, the subject carries the genetic material of the donor, in a detectable manner.

The methods described (e.g., 100, 100*b*, 100*c*) can, however, include other suitable steps and/or enable other downstream applications.

For instance, in another specific use case, the methods can be adapted for evaluation of minimal residual disease (MRD) based upon detection of numbers of cancer cell targets present in a sample from a subject after one or more phases of cancer treatment (e.g., treatment of leukemia, treatment of lymphoma, treatment of multiple myeloma, etc.).

In another specific use case, the methods of the disclosure can be adapted for single nucleotide polymorphism genotyping (SNPtyping) to measure genetic variations of SNPs between members (e.g., members of a species). Additionally, the methods can be used for single nucleotide variant genotyping (SNVtyping) for germline DNA samples.

The methods of the disclosure can also be used for applications involving disease prediction generation and monitoring with multiplexed detection of markers of a gene expression marker panel (e.g., for pregnancy-associated complications, for other applications).

In another specific use case, the methods can be adapted for ribosomal 16S and/or ITS characterization, where current sequencing technologies are fraught with high false positive rates and/or high PCR error. In relation to the specific use case, systems, methods, and compositions described can be used to disperse a sample of 16S and/or ITS ribosomal RNA (rRNA) across a plurality of partitions (as described in more detail below), where processing materials described enable detection of regions/sequences of interest (e.g., V3 region, V4 region, V5, region, other hypervariable regions, etc.), and subsequently, for operational taxonomic unit (OTU) or amplicon sequence variant (ASV) categorizations. For instance, detection of V3, V4, and/or V5 regions can be used for bacterial microbiome analyses, fungal microbiome analyses, other microbiome analyses, rare species detection, and/or other applications. Additionally or alternatively, such rRNA characterizations can be used for antimicrobial susceptibility testing (e.g., with a sample having one or more antibiotics being assessed, combined with bacteria and materials that can be used to indicate bacteria responses to the antibiotic(s)). Additionally or alternatively, such rRNA characterizations can be used for detection of a set of pathogens (e.g., up to 30 pathogens, up to 40 pathogens, up to 50 pathogens, up to 60 pathogens, up to 70 pathogens, etc.) and quantification (e.g., in relation to detection of presence or absence of various pathogens, in relation to characterization of infectious agents and potential prognoses). Additionally or alternatively, for microbial pathogen detection/quantification, any part of microbial genomics of a sample (e.g., non-rRNA targets) can be targeted, and subsequent detection can involve detection of sample composition (e.g., microbial composition, microbiome composition, etc.) without performance of next generation sequencing (NGS). In a related use case, detection/quantification of targets of a sample in a multiplexed manner can be used to differentiate between viral, fungal, and/or microbial infections (e.g., for a respiratory illness panel).

Embodiments of the methods described can be further adapted for other applications of use.

3. Computer Systems

Figure 9:
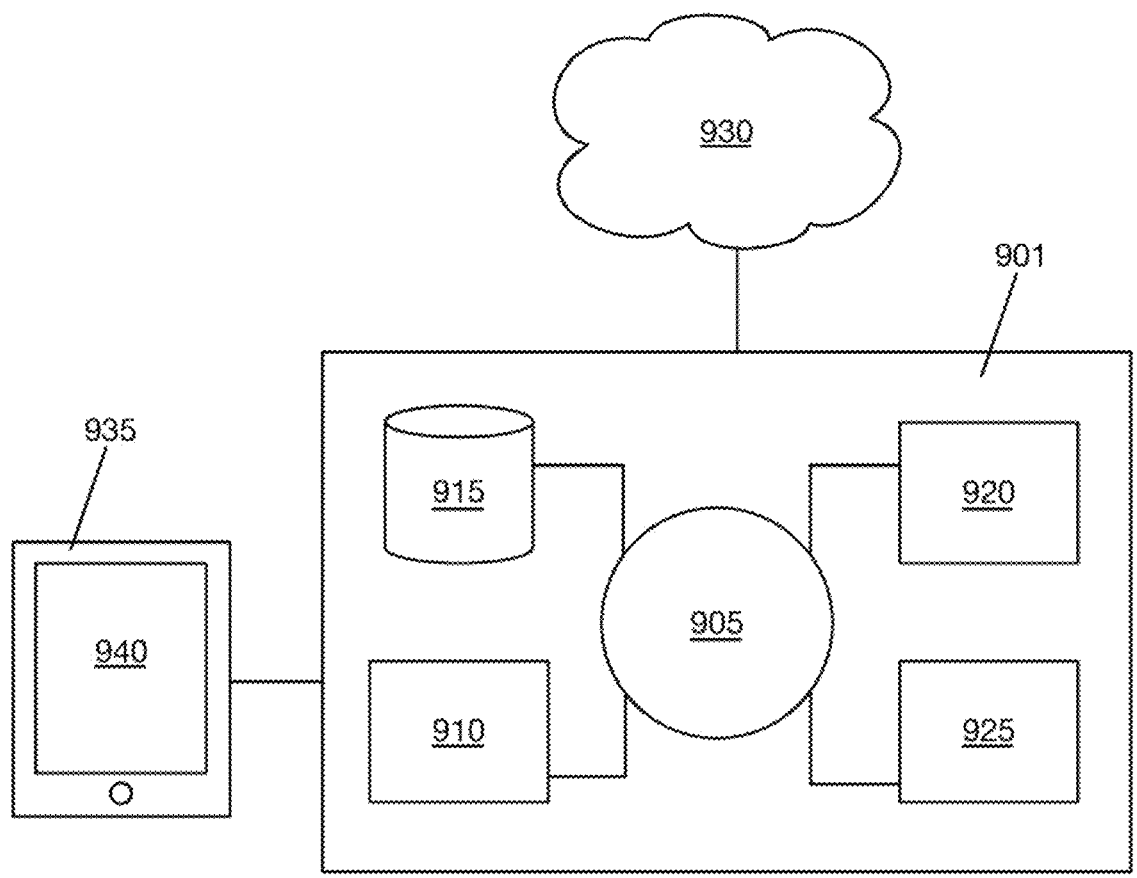
FIG. 9 illustrates a computer system that is programmed or otherwise configured to implement methods provided herein.

The present disclosure provides computer systems that are programmed to implement methods of the disclosure. FIG. 9 shows a computer system 901 that is programmed or otherwise configured to, for example, perform a digital multiplexed analysis of a sample distributed across a set of partitions, where targets are tagged using one or more multiplexing strategies described (e.g., involving color combinatorics, involving stimulus-responsive probes, involving tandem probes, involving probes that exhibit FRET behavior, with combinations of probes, with permutations of probes, etc.). Performing the digital multiplex analysis can include: reacting the sample with the set of processing materials within the set of partitions, and detecting signals from the set of partitions upon performing 3D scanning of the set of partitions with a number of color channels. In relation to color combinatorics and other multiplexing strategies described, signals from specific targets can correspond with a set of color combinatorics paired with targets of a set of targets potentially represented in the sample and contained within partitions of the set of partitions, and the set of targets can have a total number greater than the number of color channels used to detect colors corresponding to the set of color combinatorics. The digital multiplexed analysis can have SNR performance achievable as described.

The computer system 901 can additionally or alternatively perform other aspects of digital multiplexed assays for characterizations involving other loci of interest, with applications of use described above.

The computer system 901 can regulate various aspects of analysis, calculation, and generation of the present disclosure, such as, for example, generating a plurality of partitions (e.g., from an aqueous mixture including sample material and materials for an amplification reaction) within a collecting container at a desired rate, transmitting heat to and from the plurality of partitions within the collecting container, performing an optical interrogation operation with the plurality of partitions within the collecting container, and/or performing one or more digital multiplexed assay steps. The computer system 901 can be an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet.

In some embodiments, the network 930 is a telecommunication and/or data network. The network 930 can include one or more computer servers, which can enable distributed computing, such as cloud computing. For example, one or more computer servers may enable cloud computing over the network 930 ("the cloud") to perform various aspects of analysis, calculation, and generation of the present disclosure, such as, for example, generating a plurality of droplets within a collecting container at a predetermined rate or variation in polydispersity. Such cloud computing may be provided by cloud computing platforms such as, for example, Amazon Web Services (AWS), Microsoft Azure, Google Cloud Platform, and IBM cloud. In some embodiments, the network 930, with the aid of the computer system 901, can implement a peer-to-peer network, which may enable devices coupled to the computer system 901 to behave as a client or a server.

The CPU 905 may comprise one or more computer processors and/or one or more graphics processing units (GPUs). The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some embodiments, the circuit is an application specific integrated circuit (ASIC).

The storage unit 915 can store files, such as drivers, libraries and saved programs. The storage unit 915 can store user data, e.g., user preferences and user programs. In some embodiments, the computer system 901 can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 6oi can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine-readable code can be provided in the form of software. During use, the code can be executed by the processor 905. In some embodiments, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Embodiments of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, or disk drives, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, a visual display indicative of stages of or results from performing a digital multiplexed analysis of a sample distributed across a set of partitions, where targets are tagged using one or more multiplexing strategies described (e.g., involving color combinatorics, involving stimulus-responsive probes, involving tandem probes, involving probes that exhibit FRET behavior, with combinations of probes, with permutations of probes, etc.). Performing the digital multiplex analysis can include: reacting the sample with the set of processing materials within the set of partitions, and detecting signals from the set of partitions upon performing 3D scanning of the set of partitions with a number of color channels. The UI 940 can additionally or alternatively be adapted for performing other digital assays involving other loci of interests and/or other calculations, as described. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, generate a plurality of droplets within a collecting container with desired characteristics.

4. Conclusion

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

As a person skilled in the art will recognize from the previous detailed description and from the figures and claims, modifications and changes can be made to the preferred embodiments of the invention without departing from the scope of this invention defined in the following claims.

What is claimed is:

1. A method comprising:
performing a digital multiplexed analysis of a sample distributed across a set of partitions comprising more than 500,000 partitions retained in position along three axes within a closed container, wherein upon performing a set of processes, the digital multiplexed analysis has a signal-to-noise ratio (SNR) greater than $10^4$, and wherein the set of processes comprises:
reacting the sample with the set of processing materials within the set of partitions, and
detecting signals from the set of partitions upon performing 3D scanning of the set of partitions with a number of color channels,
wherein said signals correspond to a set of color combinatorics paired with targets of a set of targets potentially represented in the sample and contained within partitions of the set of partitions, and wherein the set of targets has a total number greater than the number of color channels used to detect colors corresponding to the set of color combinatorics, and wherein the number of color channels comprises at least 4 color channels.

2. The method of claim 1, wherein the digital multiplexed analysis has a dynamic range of at least $10^6$.

3. The method of claim 1, wherein the set of partitions comprises droplets of an emulsion within the closed container, and wherein the set of color combinatorics comprises combinations of up to 6 colors detectable from each of the set of partitions.

4. The method of claim 1, wherein the set of processing materials comprise, for a target of the set of targets:
a primer set comprising: a common primer and a set of target-specific primers structured to interact with a target region of the target, the set of target-specific primers comprising a first target-specific primer comprising a first flanking sequence, and
a first fluorophore-labeled oligonucleotide corresponding to the flanking sequence, the first fluorophore-labeled oligonucleotide comprising a first fluorophore configured to transmit a first target signal if the target region is amplified.

5. The method of claim 4, wherein the set of target-specific primers further comprises a second target-specific primer comprising a second flanking sequence, and the set of processing materials further comprises a second fluorophore-labeled oligonucleotide corresponding to the second flanking sequence, the second fluorophore-labeled oligonucleotide comprising a second fluorophore configured to transmit a second target signal if the target region is amplified, such that the target can be positively detected based upon the first target signal and the second target signal.

6. The method of claim 1, wherein the set of processing materials comprise, for a target of the set of targets:
a primer set comprising: at least one primer structured to tag the target with a first probe having a first fluorophore and a second probe having a second fluorophore, wherein the first fluorophore and the second fluorophore correspond to two color channels of the number of color channels.

7. The method of claim 6, further comprising causing Foerster resonance energy transfer (FRET) from the first fluorophore to the second fluorophore upon exciting the first fluorophore with a first wavelength profile of light, wherein detecting signals from the set of partitions with the number of color channels comprises detecting the target from a partition upon scanning the set of partitions with a second wavelength profile of light corresponding to an emission spectrum of the second fluorophore.

8. The method of claim 1, wherein the set of processing materials comprise, for a first target and a second target of the set of targets:
a primer set comprising: at least one primer structured to tag the first target with a first probe having a first fluorophore and the second target with a second probe having a second fluorophore.

9. The method of claim 8, wherein the first fluorophore is a photo-bleachable fluorophore, and wherein detecting signals from the set of partitions comprises scanning the set of partitions with a first wavelength range of light and a second wavelength range of light configured to bleach the first fluorophore, the method further comprising:
detecting signals from the set of partitions in a first phase of analysis upon scanning the set of partitions with the first wavelength range of light, and
detecting signals from the set of partitions in a second phase of analysis upon scanning the set of partitions and bleaching the first fluorophore with the second wavelength range of light, thereby enabling differential detection of the first target and the second target.

10. The method of claim 1, wherein the set of processing materials comprise, for a first target and a second target of the set of targets: a primer set comprising: a first primer structured to tag the first target with a first probe having a first fluorophore and a second primer structured to tag the second target with a second probe having a second fluorophore, wherein the first fluorophore is a photo-bleachable fluorophore, and wherein detecting signals from the set of partitions comprises scanning the set of partitions with a first wavelength range of light and a second wavelength range of light configured to bleach the first fluorophore, thereby enabling differential detection of the first target and the second target.

11. The method of claim 1, wherein the set of processing materials further comprises a probe additive reagent structured to reduce background noise.

12. The method of claim 11, wherein the probe additive reagent includes probe additives having a melting temperature greater than 55° C.

13. The method of claim 11, wherein the probe additive reagent comprises a quencher structured to interact with at least one of the 3' region and the 5' region of the first fluorophore-labeled oligonucleotide.

14. The method of claim 1, wherein performing the set of processes comprises determining the SNR upon:
scanning a set of planes of the set of partitions,
determining a target signal value and a noise signal value for the set of planes, and
determining the SNR from the target signal value and the noise signal value.

15. The method of claim 14,
wherein determining the target signal value and the noise signal value comprises, for a plane of the set of planes:
determining a categorization of a set of categorizations based upon a profile of signal-positive partitions represented in the plane,
determining a target signal distribution for the plane based upon the categorization, and
determining a noise signal distribution based upon the categorization, wherein the SNR is determined from the target signal distribution and the noise signal distribution.

16. The method of claim 15, wherein the set of categorizations correspond to different profiles of a set of profiles of signal-positive partitions observable in the set of planes.

17. The method of claim 14, wherein the noise signal value is attributed to fluorescence from adjacent partitions and adjacent planes of the set of planes.

18. The method of claim 1, wherein the set of partitions comprises greater than 500,000 partitions and wherein the set of partitions is characterized by less than 15% occupancy of partitions by said biological targets.

19. The method of claim 1, wherein the set of processing materials comprises a set of non-hydrolysis probes, the method further comprising tagging the set of targets with a set of permutations of the set of non-hydrolysis probes, wherein detecting signals from the set of partitions comprises detecting signals corresponding to the set of permutations for differential detection of the set of targets.

20. The method of claim 1, wherein the set of processing materials comprises a set of hydrolysis probes, the method further comprising tagging the set of targets with a set of combinations of the set of hydrolysis probes, wherein detecting signals from the set of partitions comprises detecting signals corresponding to the set of combinations for differential detection of the set of targets.

21. The method of claim 1, further comprising returning an output supporting at least one of: pathogen detection, non-invasive prenatal testing, organ transplantation analysis, forensics, and oncology, based upon the quantitative analysis.

22. The method of claim 1, wherein the set of targets comprise hypervariable regions of at least one of 16S rRNA and ITS rRNA.

* * * * *